US009518129B2

(12) United States Patent
Huntington et al.

(10) Patent No.: US 9,518,129 B2
(45) Date of Patent: Dec. 13, 2016

(54) THROMBIN-BINDING ANTIBODY MOLECULES AND USES THEREOF

(71) Applicant: Janssen Pharmaceuticals, Inc., Titusville, NJ (US)

(72) Inventors: James Andrew Huntington, Cambridge (GB); Trevor Baglin, Cambridge (GB); Jonathan Langdown, Cambridge (GB)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 61 days.

(21) Appl. No.: 14/363,514

(22) PCT Filed: Dec. 14, 2012

(86) PCT No.: PCT/GB2012/053140
§ 371 (c)(1),
(2) Date: Jun. 6, 2014

(87) PCT Pub. No.: WO2013/088164
PCT Pub. Date: Jun. 20, 2013

(65) Prior Publication Data
US 2014/0370008 A1  Dec. 18, 2014

(30) Foreign Application Priority Data

Dec. 14, 2011 (GB) .................................. 1121513.4

(51) Int. Cl.
*A61K 39/395* (2006.01)
*C07K 16/40* (2006.01)
*C07K 16/36* (2006.01)

(52) U.S. Cl.
CPC ............... *C07K 16/40* (2013.01); *C07K 16/36* (2013.01); *C07K 2317/34* (2013.01); *C07K 2317/55* (2013.01); *C07K 2317/70* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,196,404 A | 3/1993 | Maraganore et al. |
| 5,240,913 A | 8/1993 | Maraganore et al. |
| 5,433,940 A | 7/1995 | Maraganore et al. |
| 5,985,833 A | 11/1999 | Mosesson et al. |
| 7,998,939 B2 | 8/2011 | Diener et al. |
| 8,568,724 B2 | 10/2013 | Hack |

FOREIGN PATENT DOCUMENTS

| | | |
|---|---|---|
| EP | 0 489 070 B1 | 4/1996 |
| EP | 0 529 031 B1 | 5/2000 |
| WO | 91/17258 A1 | 11/1991 |
| WO | 92/01047 A1 | 1/1992 |
| WO | 98/00443 A1 | 1/1998 |
| WO | 01/00667 A2 | 1/2001 |
| WO | 01/07072 A1 | 2/2001 |
| WO | 02/17711 A2 | 3/2002 |
| WO | 03/003988 A2 | 1/2003 |
| WO | 2007/106893 A2 | 9/2007 |
| WO | 2008/155658 A2 | 12/2008 |
| WO | 2010/033167 | 3/2010 |
| WO | 2013/014092 A1 | 1/2013 |

OTHER PUBLICATIONS

Arnaud et al., Blood. Sep. 15, 1994;84(6):1843-50.*
Baerga-Ortiz et al., Protein Sci. Jun. 2002;11(6):1300-8.*
Holliger et al., Nat Biotechnol. Sep. 2005;23(9):1126-36.*
Rudikoff et al., Proc Natl Acad Sci U S A. Mar. 1982;79(6):1979-83.*
Portolano et al., J Immunol. Feb. 1, 1993 ;150(3):880-7.*
Janeway et al., Immunobiology, 3rd ed., Current Biology, 1997, pp. 3:1-3:11.*
Fundamental Immunology, W. Paul, ed., Raven Press, 1993, p. 242.*
Chouhan et al., Thromb Haemost. Feb. 1997;77(2):343-9.*
Hwang et al., J Immunol. Dec. 15, 2001;167(12):7192-8.*
Zehnder et al., Blood. Nov. 15, 1990;76(10):2011-6.*
Arnaud, E. et al., "An Autoantibody Directed Against Human Thrombin Anion-Binding Exosite in a Patient with Arterial Thrombosis: Effects on Platelets, Endothelial Cells, and Protein C Activation", Blood (1994), vol. 84:6, pp. 1843-1850.
Baegra-Ortiz, A. et al., "Two different proteins that compete for binding to thrombin have opposite kinetic and thermodynamic profiles", Protein Science (2004), vol. 13, pp. 166-176.
Chang, A.C. et al., The Reaction of Thrombin With Platelet-Derived Nexin Requires A Secondary Recognition Site in Addition To The Catalytic Site, Biochem. Biophys. Res. Comm. (1991), vol. 177:3, pp. 1198-1204.
Cook, J.J. et al., "An Antibody Against the Exosite of the Cloned Thrombin Receptor Inhibits Experimental Arterial Thrombosis in the African Green Monkey", Circulation (1995), vol. 91, pp. 2961-2971.
Guillin, M. et al., "Thrombin Specificity" Thrombosis and Haemostasis (1995), vol. 74:1, pp. 129-133.
Huntington, J.A. "Structural Insights into the Life History of Thrombin", chapter in Recent Advances in Thrombosis and Hemostasis (2008), pp. 80-106.
Huntington, J.A. "Molecular Recognition Mechanisms of Thrombin", Journal of Thrombosis and Haemostasis (2005), vol. 3, pp. 1861-1872.
Kontiola, A. et al., "Glycosyolation Pattern of Kappa Light Chains in Massive Cutaneous Hyalinosis", Glycoconjugate J. (1987), vol. 4, pp. 297-305.
Lechtenberg, B.C. et al., "NMR resonance assignments of thrombin reveal the conformational and dynamic effects of ligation", PNAS (2010), vol. 107:32, pp. 14087-14092.

(Continued)

*Primary Examiner* — Michael Szperka
(74) *Attorney, Agent, or Firm* — Stradley Ronon Stevens & Young, LLP

(57) ABSTRACT

This invention relates to isolated antibodies which recognize the exosite 1 epitope of thrombin and selectively inhibit thrombin without promoting bleeding. These antibody molecules may be useful in the treatment and prevention of thrombosis, embolism and other conditions mediated by thrombin.

25 Claims, 19 Drawing Sheets

(56) References Cited

OTHER PUBLICATIONS

Licari, L.G. et al., "Thrombin physiology and pathophysiology", Journal of Veterinary Emergency and Critical Care (2009), vol. 19:1, pp. 11-22.

Mackman, N., "Triggers, targets and treatments for thrombosis", Insight Review, Nature Publishing Group (2008), pp. 914-918.

Mushunje, A. et al., "Heparin-induced substrate behavior of antithrombin Cambridge II", Blood (2003), vol. 102:12, pp. 4028-4034.

Nimjee, S.M. et al. "Synergistic effect of aptamers that inhibit exosites 1 and 2 on thrombin", RNA (2009), vol. 15, pp. 2105-2111.

Omtvedt, L.A. et al., "Glycosylation of immunoglobulin light chains associated with amyloidosis", Amyloid: Int. J. Exp. Clin. Invest. (2000), vol. 7, pp. 227-244.

Qian, T., et al., "Structural characterization of N-linked oligosaccharides on monoclonal antibody cetuximab by the combination of orthogonal matrix-assisted laser desorption/ionization hybrid quadrupole-quadrupole time-of-flight tandem mass spectrometry and sequential enzymatic digestion", Analytical Biochemistry (2007), vol. 364, pp. 8-18.

Schumacher, W.A., et al., "Comparison of Thrombin Active Site and Exosite Inhibitors and Heparin in Experimental Models of Arterial and Venous Thrombosis and Bleeding", The Journal of Pharmacology and Experimental Therapeutics (1993), vol. 267:3, pp. 1237-1242.

Seiler, S.M. et al., "Involvement of the 'Tethered-Ligand' Receptor in Thrombin Inhibition of Platelet Adenylate Cyclase", Biochemical and Biophysical Research Communications (1992), vol. 182:3, pp. 1296-1302.

Seiler, S.M. et al., "Multiple Pathways of Thrombin-Induced Platelet Activation Differentiated by Desensitization and a Thrombin Exosite Inhibitor", Biochemical and Biophysical Research Communications (1991), vol. 181:2, pp. 636-643.

Tachibana, H. et al., "Building high affinity human antibodies by altering the glycosylation on the light chain variable region in N-acetylglucosamine-supplemented hybridoma cultures", Cytotechnology (1997), vol. 23, pp. 151-159.

Tanaka, M. et al., "O-linked glucosylation of a therapeutic recombinant humanised monoclonal antibody produced in CHO cells", European Journal of Pharmaceutics and Biopharmaceutics (2013), vol. 83, pp. 123-130.

Wu, Q. et al., "Activation-induced Exposure of the Thrombin Anion-binding Exosite", The Journal of Biological Chemistry (1994), vol. 269:5, pp. 3725-3730.

International Preliminary Report on Patentability dated Jun. 17, 2014 from PCT/GB2012/053140, 8 pgs.

International Search Report dated Apr. 29, 2013 from PCT/GB2012/053140, 6 pgs.

Search Report dated Jan. 26, 2011 from GB1015790.7, 1 pg.

Costa, J.M. et al., "Partial Characterization of an Autoantibody Recognizing the Secondary Binding Site(s) of Thrombin in a Patient with Recurrent Spontaneous Arterial Thrombosis" Thrombosis and Haemostasis (1992), vol. 67:2, pp. 193-199.

EPO Office Action issued Jul. 23, 2015 in corresponding EP Application No. 12806641.

Mollica, et al., "Antibodies to thrombin directed against both of its cryptic exosites", British Journal of Haematology, 2005, 132: 487-493.

\* cited by examiner

A

B

THROMBIN-BINDING ANTIBODY MOLECULES AND USES THEREOF

This invention relates to antibody molecules that inhibit thrombin.

REFERENCE TO A SEQUENCE LISTING

This application includes a Sequence Listing submitted electronically as a text file named Thrombin_ST25, created on Jan. 25, 2016 with a size of 8800 bytes. The Sequence Listing is incorporated by reference herein.

Blood coagulation is a key process in the prevention of bleeding from damaged blood vessels (haemostasis). However, a blood clot that obstructs the flow of blood through a vessel (thrombosis) or breaks away to lodge in a vessel elsewhere in the body (thromboembolism) can be a serious health threat.

A number of anticoagulant therapies are available to treat pathological blood coagulation. A common drawback of these therapies is an increased risk of bleeding (Mackman (2008) Nature 451(7181): 914-918). Many anticoagulant agents have a narrow therapeutic window between the dose that prevents thrombosis and the dose that induces bleeding. This window is often further restricted by variations in the response in individual patients.

The present invention relates to the unexpected finding that antibody molecules which recognise the exosite 1 epitope of thrombin selectively inhibit thrombin without promoting bleeding. These antibody molecules may be useful in the treatment and prevention of thrombosis, embolism and other conditions mediated by thrombin.

An aspect of the invention provides an isolated antibody molecule that specifically binds to exosite 1 of thrombin.

Isolated anti-exosite 1 antibody molecules may inhibit thrombin in vivo without promoting or substantially promoting bleeding or haemorrhage, i.e. the antibody molecules do not inhibit or substantially inhibit normal physiological responses to vascular injury (i.e. haemostasis). For example, haemostasis may not be inhibited or may be minimally inhibited by the antibody molecules (i.e. inhibited to an insignificant extent which does not affect the well-being of patient or require further intervention). Bleeding may not be increased or may be minimally increased by the antibody molecules.

Exosite 1 (also known as 'anion binding exosite 1' and the 'fibrinogen recognition exosite') is a well-characterised secondary binding site on the thrombin molecule (see for example James A. Huntington, 2008, Structural Insights into the Life History of Thrombin, in Recent Advances in Thrombosis and Hemostasis 2008, editors; K. Tanaka and E. W. Davie, Springer Japan KK, Tokyo, pp. 80-106). Exosite 1 is formed in mature thrombin but is not formed in prothrombin (see for example Anderson et al (2000) JBC 2775 16428-16434).

Exosite 1 is involved in recognising thrombin substrates, such as fibrinogen, but is remote from the catalytic active site. Various thrombin binding factors bind to exosite 1, including the anticoagulant dodecapeptide hirugen (Naski et al 1990 JBC 265 13484-13489), factor V, factor VIII, thrombomodulin (cofactor for protein C and TAFI activation), fibrinogen, PAR1 and fibrin (the co-factor for factor XIII activation).

An anti-exosite 1 antibody may bind to exosite 1 of mature human thrombin. The sequence of human preprothrombin is set out in SEQ ID NO: 1. Human prothrombin has the sequence of residues 44 to 622 of SEQ ID NO: 1. Mature human thrombin has the sequence of residues 314-363 (light chain) and residues 364 to 622 (heavy chain).

In some embodiments, an anti-exosite 1 antibody may also bind to exosite 1 of mature thrombin from other species. Thrombin sequences from other species are known in the art and available on public databases such as Genbank. The corresponding residues in thrombin sequences from other species may be easily identified using sequence alignment tools.

The numbering scheme for thrombin residues set out herein is conventional in the art and is based on the chymotrypsin template (Bode W et al EMBO J. 1989 November; 8(11):3467-75). Thrombin has insertion loops relative to chymotrypsin that are lettered sequentially using lower case letters.

Exosite 1 of mature human thrombin is underlined in SEQ ID NO: 1 and may include the following residues: M32, F34, R35, K36, S36a, P37, Q38, E39, L40, L65, R67, S72, R73, T74, R75, Y76, R77a, N78, E80, K81, I82, S83, M84, K109, K110, K149e, G150, Q151, S153 and V154. In some embodiments, other thrombin residues which are located close to (i.e. within 0.5 nm or within 1 nm) of any one of these residues may also be considered to be part of exosite 1.

An anti-exosite 1 antibody may bind to an epitope which comprises 1, 2, 3, 4, 5, 6, 7, 8, 9, 10, 11, 12, 13, 14, 15, 16, 17, 18, 19, 20 or more than 20 residues of exosite 1. Preferably, an anti-exosite 1 antibody binds to an epitope which consists entirely of exosite 1 residues.

For example, an anti-exosite 1 antibody may bind to an epitope which comprises 1, 2, 3, 4, 5, 6, 7, 8, 9, 10, 11, 12, 13, 14, 15 or all 16 residues selected from the group consisting of M32, F34, S36a, P37, Q38, E39, L40, L65, R67, R73, T74, R75, Y76, R77a, I82 and Q151 of human thrombin or the equivalent residues in thrombin from another species. In some preferred embodiments, the epitope may comprise the thrombin residues Q38, R73, T74, Y76 and R77a and optionally one or more additional residues.

Anti-exosite 1 antibody molecules as described herein are specific for thrombin exosite 1 and bind to this epitope with high affinity relative to other epitopes, for example epitopes from mammalian proteins other than mature thrombin. For example, an anti-exosite 1 antibody molecule may display a binding affinity for thrombin exosite 1 which is at least 500 fold, at least 1000 fold or at least 2000 fold greater than other epitopes.

Preferably, an antibody molecule as described herein which is specific for exosite 1 may bind to mature thrombin but display no binding or substantially no binding to prothrombin.

Without being bound by any theory, anti-exosite 1 antibodies may be unable to access thrombin within the core of a haemostatic clot, and are therefore unable to affect haemostasis by interrupting normal thrombin function at sites of vascular injury. However, because the anti-exosite 1 antibodies still bind to thrombin on the surface of the clot and in the outer shell of the clot, thrombosis is prevented, i.e. non-haemostatic clot extension is prevented.

An anti-exosite 1 antibody molecule may have a dissociation constant for exosite 1 of less than 50 nM, less than 40 nM, less than 30 nM, less than 20 nM, less than 10 nM, or less than 1 nM. For example, an antibody molecule may have an affinity for exosite 1 of 0.1 to 50 nM, e.g. 0.5 to 10 nM. A suitable anti-exosite 1 antibody molecule may, for example, have an affinity for thrombin exosite 1 of about 1 nM.

Binding kinetics and affinity (expressed as the equilibrium dissociation constant, $K_d$) of the anti-exosite 1 antibody molecules may be determined using standard techniques, such as surface plasmon resonance e.g. using BIAcore analysis.

An anti-exosite 1 antibody molecule as described herein may be an immunoglobulin or fragment thereof, and may be natural or partly or wholly synthetically produced, for example a recombinant molecule.

Anti-exosite 1 antibody molecules may include any polypeptide or protein comprising an antibody antigen-binding site, including Fab, Fab$_2$, Fab$_3$, diabodies, triabodies, tetrabodies, minibodies and single-domain antibodies, including nanobodies, as well as whole antibodies of any isotype or sub-class. Antibody molecules and methods for their construction and use are described, in for example Holliger & Hudson, Nature Biotechnology 23(9):1126-1136 (2005).

In some preferred embodiments, the anti-exosite 1 antibody molecule may be a whole antibody. For example, the anti-exosite 1 antibody molecule may be an IgG, IgA, IgE or IgM or any of the isotype sub-classes, particularly IgG1 and IgG4. The anti-exosite 1 antibody molecules may be monoclonal antibodies. In other preferred embodiments, the anti-exosite 1 antibody molecule may be an antibody fragment.

Anti-exosite 1 antibody molecules may be chimeric, humanised or human antibodies.

Anti-exosite 1 antibody molecules as described herein may be isolated, in the sense of being free from contaminants, such as antibodies able to bind other polypeptides and/or serum components. Monoclonal antibodies are preferred for some purposes, though polyclonal antibodies may also be employed.

Anti-exosite 1 antibody molecules may be obtained using techniques which are standard in the art. Methods of producing antibodies include immunizing a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al., 1992, Nature 357: 80-82). Isolation of antibodies and/or antibody-producing cells from an animal may be accompanied by a step of sacrificing the animal.

As an alternative or supplement to immunizing a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Other anti-exosite 1 antibody molecules may be identified by screening patient serum for antibodies which bind to exosite 1.

In some embodiments, anti-thrombin antibody molecules may be produced by any convenient means, for example a method described above, and then screened for differential binding to mature thrombin relative to thrombin with an exosite 1 mutation, gamma thrombin (exosite 1 defective due to autolysis at R75 and R77a) or prothrombin. Suitable screening methods are well-known in the art.

An antibody which displays increased binding to mature thrombin, relative to non-thrombin proteins, thrombin with an exosite 1 mutation, gamma-thrombin or prothrombin, for example an antibody which binds to mature thrombin but does not bind to thrombin with an exosite I mutation, gamma thrombin or prothrombin, may be identified as an anti-exosite 1 antibody molecule.

After production and/or isolation, the biological activity of an anti-exosite 1 antibody molecule may be tested. For example, the ability of the antibody molecule to inhibit thrombin substrate, cofactor or inhibitor binding and/or cleavage by thrombin may be determined and/or the ability of the antibody molecule to inhibit thrombosis without promoting bleeding may be determined.

Suitable antibody molecules may be tested for activity using a fibrinogen clotting or thrombin time assay. Suitable assays are well-known in the art.

The effect of an antibody molecule on coagulation and bleeding may be determined using standard techniques. For example, the effect of an antibody molecule on thrombosis may be determined in an animal model, such as a mouse model with ferric chloride induced clots in blood vessels. Effects on haemostasis may also be determined in an animal model, for example, by measuring tail bleed of a mouse.

Antibody molecules normally comprise an antigen binding domain comprising an immunoglobulin heavy chain variable domain (VH) and an immunoglobulin light chain variable domain (VL), although antigen binding domains comprising only a heavy chain variable domain (VH) are also possible (e.g. camelid or shark antibodies).

Each of the VH and VL domains typically comprise three complementarity determining regions (CDRs) responsible for antigen binding, interspersed by framework regions.

In some embodiments, binding to exosite 1 may occur wholly or substantially through the VHCDR3 of the anti-exosite 1 antibody molecule.

For example, an anti-exosite 1 antibody molecule may comprise a VH domain comprising a HCDR3 having the amino acid sequence of SEQ ID NO: 5 or the sequence of SEQ ID NO: 5 with 1 or more, for example 2, 3, 4 or 5 or more amino acid substitutions, deletions or insertions. The substitutions may be conservative substitutions. In some embodiments, the HCDR3 may comprise the amino acid residues at positions 4 to 9 of SEQ ID NO: 5 (SEFEPF), or more preferably the amino acid residues at positions 2, and 4 to 10 of SEQ ID NO: 5 (D and SEFEPFS) with substitutions, deletions or insertions at one or more other positions in SEQ ID NO:5. The HCDR3 may be the only region of the antibody molecule that interacts with a thrombin exosite 1 epitope or substantially the only region. The HCDR3 may therefore determine the specificity and/or affinity of the antibody molecule for the exosite 1 region of thrombin.

The VH domain of an anti-exosite 1 antibody molecule may additionally comprise an HCDR2 having the amino acid sequence of SEQ ID NO: 4 or the sequence of SEQ ID NO: 4 with 1 or more, for example 2, 3, 4 or 5 or more amino acid substitutions, deletions or insertions. In some embodiments, the HCDR2 may comprise the amino acid residues at positions 3 to 7 of SEQ ID NO: 4 (DPQDG) or the amino acid residues at positions 2 and 4 to 7 of SEQ ID NO: 4 (L and PQDG) of SEQ ID NO: 4, with substitutions, deletions or insertions at one or more other positions in SEQ ID NO: 4.

The VH domain of an anti-exosite 1 antibody molecule may further comprise an HCDR1 having the amino acid sequence of SEQ ID NO: 3 or the sequence of SEQ ID NO: 3 with 1 or more, for example 2, 3, 4 or 5 or more amino acid substitutions, deletions or insertions. In some embodiments, the HCDR1 may comprise amino acid residue T at position 5 of SEQ ID NO: 3 with substitutions, deletions or insertions at one or more other positions in SEQ ID NO: 3.

In some embodiments, an antibody molecule may comprise a VH domain comprising a HCDR1, a HCDR2 and a HCDR3 having the sequences of SEQ ID NOs 3, 4 and 5 respectively. For example, an antibody molecule may comprise a VH domain having the sequence of SEQ ID NO: 2 or the sequence of SEQ ID NO: 2 with 1 or more, for example 2, 3, 4, 5, 6, 7, 8, 9, 10 or more amino acid substitutions, deletions or insertions in SEQ ID NO: 2.

The anti-exosite 1 antibody molecule may further comprise a VL domain, for example a VL domain comprising LCDR1, LCDR2 and LCDR3 having the sequences of SEQ ID NOs 7, 8 and 9 respectively, or the sequences of SEQ ID NOs 7, 8 and 9 respectively with, independently, 1 or more, for example 2, 3, 4 or 5 or more amino acid substitutions, deletions or insertions. The substitutions may be conservative substitutions. For example, an antibody molecule may comprise a VL domain having the sequence of SEQ ID NO: 6 or the sequence of SEQ ID NO: 6 with 1 or more, for example 2, 3, 4, 5, 6, 7, 8, 9, 10 or more amino acid substitutions, deletions or insertions in SEQ ID NO: 6.

In some embodiments, the VL domain may comprise Tyr49.

The anti-exosite 1 antibody molecule may for example comprise one or more amino acid substitutions, deletions or insertions which improve one or more properties of the antibody, for example affinity, functional half-life, on and off rates.

The techniques that are required in order to introduce substitutions, deletions or insertions within amino acid sequences of CDRs, antibody VH or VL domains and antibodies are generally available in the art. Variant sequences may be made, with substitutions, deletions or insertions that may or may not be predicted to have a minimal or beneficial effect on activity, and tested for ability to bind exosite 1 of thrombin and/or for any other desired property.

In some embodiments, anti-exosite 1 antibody molecule may comprise a VH domain comprising a HCDR1, a HCDR2 and a HCDR3 having the sequences of SEQ ID NOs 3, 4, and 5, respectively, and a VL domain comprising a LCDR1, a LCDR2 and a LCDR3 having the sequences of SEQ ID NOs 7, 8 and 9, respectively.

For example, the VH and VL domains may have the amino acid sequences of SEQ ID NO: 2 and SEQ ID NO: 6 respectively; or may have the amino acid sequences of SEQ ID NO: 2 and SEQ ID NO: 6 comprising, independently 1 or more, for example 2, 3, 4, 5, 6, 7, 8, 9, 10 or more amino acid substitutions, deletions or insertions. The substitutions may be conservative substitutions.

In some embodiments, an antibody may comprise one or more substitutions, deletions or insertions which remove a glycosylation site. For example, a glycosylation site in VL domain of SEQ ID NO 6 may be mutated out by introducing a substitution at either N28 or S30.

The anti-exosite 1 antibody molecule may be in any format, as described above, In some preferred embodiments, the anti-exosite 1 antibody molecule may be a whole antibody, for example an IgG, such as IgG1 or IgG4, IgA, IgE or IgM.

An anti-exosite 1 antibody molecule of the invention may be one which competes for binding to exosite 1 with an antibody molecule described above, for example an antibody molecule which (i) binds thrombin exosite 1 and
(ii) comprises a VH domain of SEQ ID NO: 2 and/or VL domain of SEQ ID NO: 6; an HCDR3 of SEQ ID NO: 5; an HCDR1, HCDR2, LCDR1, LCDR2, or LCDR3 of SEQ ID NOS: 3, 4, 7, 8 or 9 respectively; a VH domain comprising HCDR1, HCDR2 and HCDR3 sequences of SEQ ID NOS: 3, 4 and 5 respectively; and/or a VH domain comprising HCDR1, HCDR2 and HCDR3 sequences of SEQ ID NOS: 3, 4 and 5 and a VL domain comprising LCDR1, LDR2 and LCDR3 sequences of SEQ ID NOS: 7, 8 and 9 respectively.

Competition between antibody molecules may be assayed easily in vitro, for example using ELISA and/or by tagging a specific reporter molecule to one antibody molecule which can be detected in the presence of one or more other untagged antibody molecules, to enable identification of antibody molecules which bind the same epitope or an overlapping epitope. Such methods are readily known to one of ordinary skill in the art. Thus, a further aspect of the present invention provides an antibody molecule comprising a antibody antigen-binding site that competes with an antibody molecule, for example an antibody molecule comprising a VH and/or VL domain, CDR e.g. HCDR3 or set of CDRs of the parent antibody described above for binding to exosite 1 of thrombin. A suitable antibody molecule may comprise an antibody antigen-binding site which competes with an antibody antigen-binding site for binding to exosite 1 wherein the antibody antigen-binding site is composed of a VH domain and a VL domain, and wherein the VH and VL domains comprise HCDR1, HCDR2 and HCDR3 sequences of SEQ ID NOS: 3, 4, and 5 and LCDR1, LDR2 and LCDR3 sequences of SEQ ID NOS: 7, 8, and 9 respectively, for example the VH and VL domains of SEQ ID NOS: 2 and 6.

An anti-exosite 1 antibody molecule as described herein may inhibit the binding of thrombin-binding factors, including factors which bind to exosite 1. For example, an antibody molecule may competitively or non-competitively inhibit the binding of one or more of fV, fVIII, thrombomodulin, fibrinogen or fibrin, PAR1 and/or hirugen and hirudin analogues to thrombin.

An anti-exosite 1 antibody molecule as described herein may inhibit one or more activities of thrombin. For example, an anti-exosite 1 antibody molecule may inhibit the hydrolytic cleavage of one or more thrombin substrates, such as fibrinogen, platelet receptor PAR-1 and coagulation factor FVIII. For example, binding of the antibody molecule to thrombin may result in an at least 5-fold, at least 10-fold, or at least 15-fold decrease in the hydrolysis of fibrinogen, PAR-1, coagulation factor FVIII and/or another thrombin substrates, such as factor V, factor XIII in the presence of fibrin, and protein C and/or TAFI in the presence of thrombomodulin. In some embodiments, binding of thrombin by the anti-exosite 1 antibody molecule may result in no detectable cleavage of the thrombin substrate by thrombin.

Techniques for measuring thrombin activity, for example by measuring the hydrolysis of thrombin substrates in vitro are standard in the art and are described herein.

Anti-exosite 1 antibody molecules may be further modified by chemical modification, for example by PEGylation, or by incorporation in a liposome, to improve their pharmaceutical properties, for example by increasing in vivo half-life.

The effect of an anti-exosite 1 antibody molecule on coagulation and bleeding may be determined using standard techniques. For example, the effect of an antibody on a thrombosis model may be determined. Suitable models include ferric chloride clot induction in blood vessels in a murine model, followed by a tail bleed to test normal haemostasis. Other suitable thrombosis models are well known in the art (see for example Westrick et al ATVB (2007) 27:2079-2093)

Anti-exosite 1 antibody molecules may be comprised in pharmaceutical compositions with a pharmaceutically acceptable excipient.

A pharmaceutically acceptable excipient may be a compound or a combination of compounds entering into a pharmaceutical composition which does not provoke secondary reactions and which allows, for example, facilitation of the administration of the anti-exosite 1 antibody molecule, an increase in its lifespan and/or in its efficacy in the body or an increase in its solubility in solution. These pharmaceutically acceptable vehicles are well known and will be adapted by the person skilled in the art as a function of the mode of administration of the anti-exosite 1 antibody molecule.

In some embodiments, anti-exosite 1 antibody molecules may be provided in a lyophilised form for reconstitution prior to administration. For example, lyophilised antibody molecules may be re-constituted in sterile water and mixed with saline prior to administration to an individual.

Anti-exosite 1 antibody molecules will usually be administered in the form of a pharmaceutical composition, which may comprise at least one component in addition to the antibody molecule. Thus pharmaceutical compositions may comprise, in addition to the anti-exosite 1 antibody molecule, a pharmaceutically acceptable excipient, carrier, buffer, stabilizer or other materials well known to those skilled in the art. Such materials should be non-toxic and should not interfere with the efficacy of the anti-exosite 1 antibody molecule. The precise nature of the carrier or other material will depend on the route of administration, which may be by bolus, infusion, injection or any other suitable route, as discussed below.

For parenteral, for example sub-cutaneous or intra-venous administration, e.g. by injection, the pharmaceutical composition comprising the anti-exosite 1 antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

A pharmaceutical composition comprising an anti-exosite 1 antibody molecule may be administered alone or in combination with other treatments, either simultaneously or sequentially dependent upon the condition to be treated.

An anti-exosite 1 antibody molecule as described herein may be used in a method of treatment of the human or animal body, including prophylactic or preventative treatment (e.g. treatment before the onset of a condition in an individual to reduce the risk of the condition occurring in the individual; delay its onset; or reduce its severity after onset). The method of treatment may comprise administering an anti-exosite 1 antibody molecule to an individual in need thereof.

Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners. Prescription of treatment, e.g. decisions on dosage etc, is within the responsibility of general practitioners and other medical doctors and may depend on the severity of the symptoms and/or progression of a disease being treated. Appropriate doses of antibody molecules are well known in the art (Ledermann J. A. et al. (1991) Int. J. Cancer 47: 659-664; Bagshawe K. D. et al. (1991) Antibody, Immunoconjugates and Radiopharmaceuticals 4: 915-922). Specific dosages may be indicated herein or in the Physician's Desk Reference (2003) as appropriate for the type of medicament being administered may be used. A therapeutically effective amount or suitable dose of an antibody molecule may be determined by comparing its in vitro activity and in vivo activity in an animal model. Methods for extrapolation of effective dosages in mice and other test animals to humans are known. The precise dose will depend upon a number of factors, including whether the antibody is for prevention or for treatment, the size and location of the area to be treated, the precise nature of the antibody (e.g. whole antibody, fragment) and the nature of any detectable label or other molecule attached to the antibody.

A typical antibody dose will be in the range 100 µg to 1 g for systemic applications, and 1 µg to 1 mg for topical applications. An initial higher loading dose, followed by one or more lower doses, may be administered. Typically, the antibody will be a whole antibody, e.g. the IgG1 or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. The treatment schedule for an individual may be dependent on the pharmocokinetic and pharmacodynamic properties of the antibody composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Treatment may be given before, and/or after surgery, and/or may be administered or applied directly at the anatomical site of surgical treatment or invasive procedure. Suitable formulations and routes of administration are described above.

In some embodiments, anti-exosite 1 antibody molecules as described herein may be administered as sub-cutaneous injections. Sub-cutaneous injections may be administered using an auto-injector, for example for long term prophylaxis/treatment.

In some preferred embodiments, the therapeutic effect of the anti-exosite 1 antibody molecule may persist for several half-lives, depending on the dose. For example, the therapeutic effect of a single dose of anti-exosite 1 antibody molecule may persist in an individual for 1 month or more, 2 months or more, 3 months or more, 4 months or more, 5 months or more, or 6 months or more.

Anti-exosite 1 antibody molecules described herein inhibit thrombin and may be useful in the treatment of thrombin-mediated conditions.

Haemostasis is the normal coagulation response i.e. the prevention of bleeding or haemorrhage, for example from a damaged blood vessel. Haemostasis arrests bleeding and haemorrhage from blood vessels in the body.

Anti-exosite 1 antibody molecules may have no effect or substantially no effect on haemostasis i.e. they do not promote bleeding or haemorrhage.

Aspects of the invention provide; an anti-exosite 1 antibody molecule as described herein for use in a method of treatment of the human or animal body; an anti-exosite 1 antibody molecule as described herein for use in a method of treatment of a thrombin-mediated disorder; the use of an anti-exosite 1 antibody molecule as described herein in the manufacture of a medicament for the treatment of a thrombin-mediated condition; and a method of treatment of a thrombin-mediated condition comprising administering an anti-exosite 1 antibody molecule as described herein to an individual in need thereof.

Inhibition of thrombin by anti-exosite 1 antibodies as described herein may be of clinical benefit in the treatment of any thrombin-mediated condition. A thrombin-mediated condition may include disorders associated with the formation or activity of thrombin.

Thrombin plays a key role in haemostasis, coagulation and thrombosis. Thrombin-mediated conditions include thrombotic conditions, such as thrombosis and embolism.

Thrombosis is coagulation which is in excess of what is required for haemostasis (i.e. excessive coagulation), or which is not required for haemostasis (i.e. extra-haemostatic or non-haemostatic coagulation).

Thrombosis is blood clotting within the blood vessel lumen. It is characterised by the formation of a clot (thrombus) that is in excess of requirement or not required for haemostasis. The clot may impede blood flow through the blood vessel leading to medical complications. A clot may break away from its site of formation, leading to embolism elsewhere in the circulatory system. In the arterial system, thrombosis is typically the result of atherosclerotic plaque rupture.

In some embodiments, thrombosis may occur after an initial physiological haemostatic response, for example damage to endothelial cells in a blood vessel. In other embodiments, thrombosis may occur in the absence of any physiological haemostatic response.

Thrombosis may occur in individuals with an intrinsic tendency to thrombosis (i.e. thrombophilia) or in 'normal' individuals with no intrinsic tendency to thrombosis, for example in response to an extrinsic stimulus.

Thrombosis and embolism may occur in any vein, artery or other blood vessel within the circulatory system and may include microvascular thrombosis.

Thrombosis and embolism may be associated with surgery (either during surgery or afterwards) or the insertion of foreign objects, such as coronary stents, into a patient.

For example, anti-exosite 1 antibodies as described herein may be useful in the surgical and other procedures in which blood is exposed to artificial surfaces, such as open heart surgery and dialysis.

Thrombotic conditions may include thrombophilia, thrombotic stroke and coronary artery occlusion.

Patients suitable for treatment as described herein include patients with conditions in which thrombosis is a symptom or a side-effect of treatment or which confer an increased risk of thrombosis or patients who are predisposed to or at increased risk of thrombosis, relative to the general population. For example, an anti-exosite 1 antibody molecule as described herein may also be useful in the treatment or prevention of venous thrombosis in cancer patients, and in the treatment or prevention of hospital-acquired thrombosis, which is responsible for 50% of cases of venous thromboembolism.

Anti-exosite 1 antibody molecules as described herein may exert a therapeutic or other beneficial effect on thrombin-mediated conditions, such as thrombotic conditions, without substantially inhibiting or impeding haemostasis. For example, the risk of haemorrhage in patients treated with anti-exosite 1 antibody molecules may not be increased or substantially increased relative to untreated individuals.

Individuals treated with conventional anticoagulants, such as natural and synthetic heparins, warfarin, direct serine protease inhibitors (e.g. argatroban, dabigatran, apixaban, and rivaroxaban), hirudin and its derivatives (e.g. lepirudin and bivalirudin), and anti-platelet drugs (e.g. clopidogrel, ticlopidine and abciximab) cause bleeding. The risk of bleeding in patients treated with anti-exosite 1 antibody molecules as described herein may be reduced relative to individuals treated with conventional anticoagulants.

Thrombin-mediated conditions include non-thrombotic conditions associated with thrombin activity, including inflammation, infection, tumour growth and metastasis, organ rejection and dementia (vascular and non-vascular, e.g. Alzheimer's disease) (Licari et al J Vet Emerg Crit. Care (San Antonio). 2009 February; 19(1):11-22; Tsopanoglou et al Eur Cytokine Netw. 2009 Dec. 1; 20(4):171-9).

Anti-exosite 1 antibody molecules as described herein may also be useful in in vitro testing, for example in the analysis and characterisation of coagulation, for example in a sample obtained from a patient.

Anti-exosite 1 antibody molecules may be useful in the measurement of thrombin generation. Assays of thrombin generation are technically problematic because the conversion of fibrinogen to fibrin causes turbidity, which precludes the use of a simple chromogenic end-point.

The addition of an anti-exosite 1 antibody molecule as described herein to a sample of blood prevents or inhibits fibrin formation and hence turbidity and permits thrombin generation to be measured using a chromogenic substrate, without the need for a defibrination step.

For example, a method of measuring thrombin generation may comprise contacting a blood sample with a chromogenic thrombin substrate in the presence of an anti-exosite 1 antibody molecule as described herein and measuring the chromogenic signal from the substrate;
  wherein the chromogenic signal is indicative of thrombin generation in the sample.

The chromogenic signal may be measured directly without defibrination of the sample.

Suitable substrates are well known in the art and include S2238 (H-D-Phe-Pip-Arg-pNa), β-Ala-Gly-Arg-p-nitroanilide diacetate (Prasa, D. et al. (1997) *Thromb. Haemost.* 78, 1215; Sigma Aldrich Inc) and Tos-Gly-Pro-Arg-pNa.AcOH (Biophen CS-01 (81); Aniara Inc OH USA).

Anti-exosite 1 antibody molecules may also be useful in inhibiting or preventing the coagulation of blood as described above in extracorporeal circulations, such as haemodialysis and extracorporeal membrane oxygenation.

For example, a method of inhibiting or preventing blood coagulation in vitro or ex vivo may comprise introducing an anti-exosite 1 antibody molecule as described herein to a blood sample. The blood sample may be introduced into an extracorporeal circulation system before, simultaneous with or after the introduction of the anti-exosite 1 antibody and optionally subjected to treatment such as haemodialysis or oxygenation. In some embodiments, the treated blood may be subsequently administered to an individual. Other embodiments provide an anti-exosite 1 antibody molecule as described herein for use in a method of inhibiting or preventing blood coagulation in a blood sample ex vivo and the use of an anti-exosite 1 antibody molecule as described herein in the manufacture of a medicament for use in a method of inhibiting or preventing blood coagulation in a blood sample ex vivo.

Other aspects of the invention relate to the production of antibody molecules which bind to the exosite 1 epitope of thrombin and may be useful, for example in the treatment of pathological blood coagulation or thrombosis.

A method for producing an antibody antigen-binding domain for the exosite 1 epitope of thrombin, may comprise;
  providing, by way of addition, deletion, substitution or insertion of one or more amino acids in the amino acid sequence of a parent VH domain comprising HCDR1, HCDR2 and HCDR3, wherein HCDR1, HCDR2 and HCDR3 have the amino acid sequences of SEQ ID NOS: 3, 4 and 5 respectively, a VH domain which is an amino acid sequence variant of the parent VH domain, and;
  optionally combining the VH domain thus provided with one or more VL domains to provide one or more VH/VL combinations; and
  testing said VH domain which is an amino acid sequence variant of the parent VH domain or the VH/VL combination or combinations to identify an antibody antigen binding domain for the exosite 1 epitope of thrombin.

A VH domain which is an amino acid sequence variant of the parent VH domain may have the HCDR3 sequence of SEQ ID NO: 5 or a variant with the addition, deletion, substitution or insertion of one, two, three or more amino acids.

The VH domain which is an amino acid sequence variant of the parent VH domain may have the HCDR1 and HCDR2 sequences of SEQ ID NOS: 3 and 4 respectively, or variants of these sequences with the addition, deletion, substitution or insertion of one, two, three or more amino acids.

A method for producing an antibody molecule that specifically binds to the exosite 1 epitope of thrombin may comprise:
  providing starting nucleic acid encoding a VH domain or a starting repertoire of nucleic acids each encoding a VH domain, wherein the VH domain or VH domains either comprise a HCDR1, HCDR2 and/or HCDR3 to be replaced or lack a HCDR1, HCDR2 and/or HCDR3 encoding region;
  combining said starting nucleic acid or starting repertoire with donor nucleic acid or donor nucleic acids encoding or produced by mutation of the amino acid sequence of an HCDR1, HCDR2, and/or HCDR3 having the amino acid sequences of SEQ ID NOS: 3, 4 and 5 respectively, such that said donor nucleic acid is or donor nucleic acids are inserted into the CDR1, CDR2 and/or CDR3 region in the starting nucleic acid or starting repertoire, so as to provide a product repertoire of nucleic acids encoding VH domains;
  expressing the nucleic acids of said product repertoire to produce product VH domains;
  optionally combining said product VH domains with one or more VL domains;
  selecting an antibody molecule that binds exosite 1 of thrombin, which antibody molecule comprises a product VH domain and optionally a VL domain; and
  recovering said antibody molecule or nucleic acid encoding it.

Suitable techniques for the maturation and optimisation of antibody molecules are well-known in the art.

Antibody antigen-binding domains and antibody molecules for the exosite 1 epitope of thrombin may be tested as described above. For example, the ability to bind to thrombin and/or inhibit the cleavage of thrombin substrates may be determined.

The effect of an antibody molecule on coagulation and bleeding may be determined using standard techniques. For example, a mouse thrombosis model of ferric chloride clot induction in a blood vessel, such as the femoral vein or carotid artery, followed by a tail bleed to test normal haemostasis, may be employed.

Various further aspects and embodiments of the present invention will be apparent to those skilled in the art in view of the present disclosure.

All documents mentioned in this specification are incorporated herein by reference in their entirety.

Unless stated otherwise, antibody residues are numbered herein in accordance with the Kabat numbering scheme.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described. Thus, the features set out above are disclosed in all combinations and permutations.

Certain aspects and embodiments of the invention will now be illustrated by way of example and with reference to the figures and tables described below.

FIG. 1 shows the binding and elution of the IgA on human thrombin-Sepharose column. FIG. 1A shows an elution profile for IgA (narrow peak) from a thrombin-Sepharose column using a pH gradient (neutral to low, indicated by upward sloping line). FIG. 1B shows a native blue gel showing total IgA load, flow-through from the human thrombin column and eluate following elution at low pH.

FIG. 2 shows a non-reducing SDS-PAGE gel which indicates that the IgA binds thrombin but not prothrombin. In this pull-down assay, lectin agarose is used to bind to IgA in the presence of thrombin or prothrombin. The supernatant is then run on an SDS gel. Lane 1 is size standards; lane 2 shows a depletion of thrombin from the supernatant; Lane 3 shows that depletion is dependent on the presence of the IgA; Lanes 3 and 4 show that prothrombin is not depleted, and therefore does not bind to the IgA.

Figure 10:
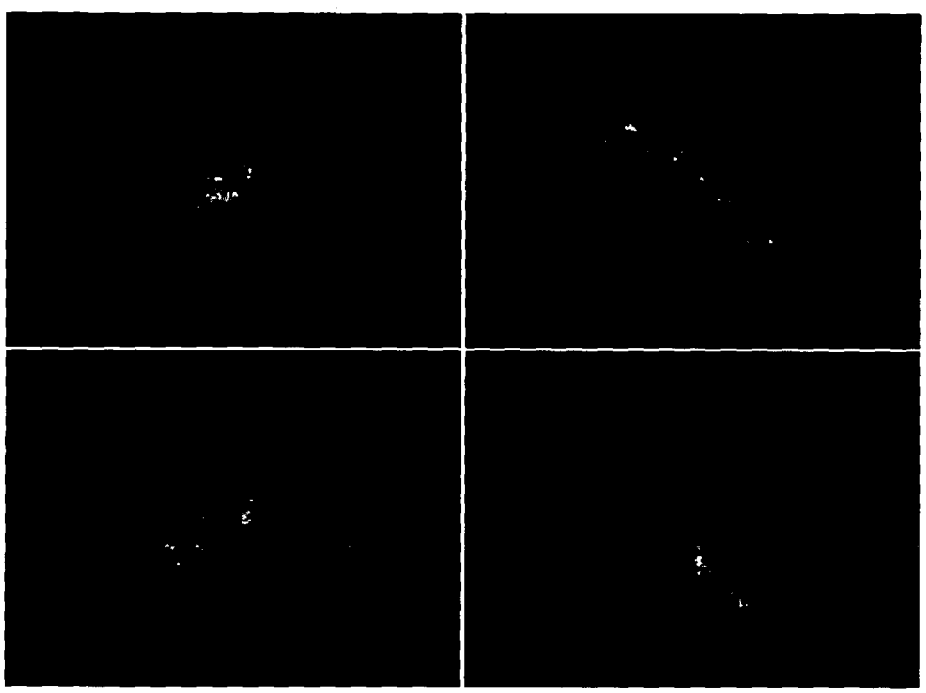

FIG. 10 shows fluorescence microscopy images of $FeCl_3$ induced blood clots in femoral vein injuries in C57BL/6 mice injected with FITC labelled fibrinogen and 40 nM (final concentration in mouse blood, equivalent to a dose of approximately 0.6 mg/Kg) anti-exosite 1 IgA (100 μl in PBS).

Figure 11:
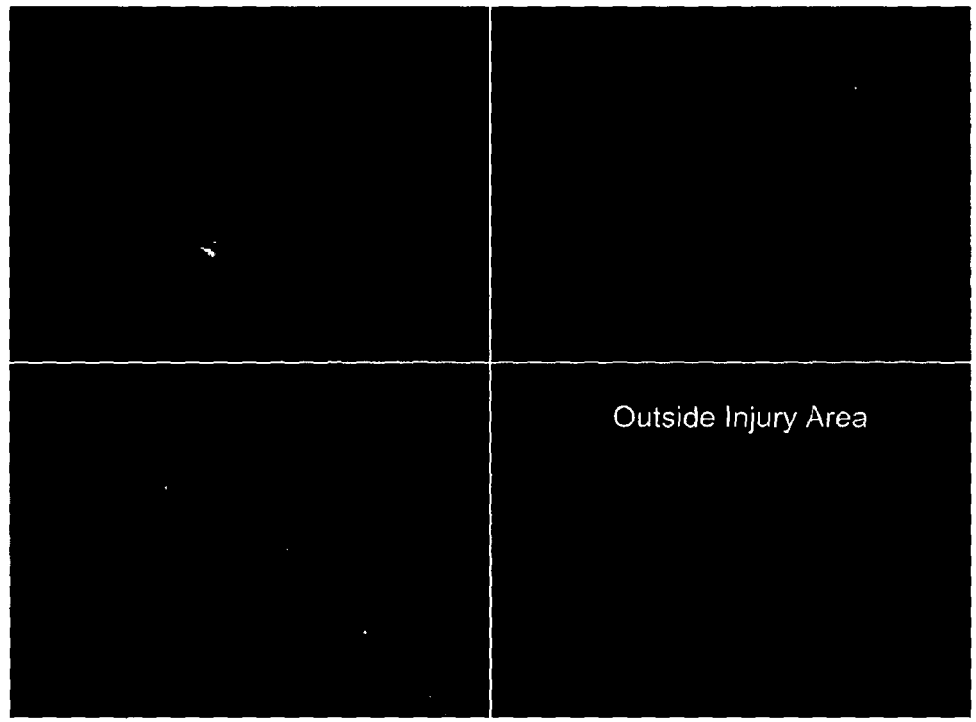

FIG. 11 shows fluorescence microscopy images of $FeCl_3$ induced blood clots in femoral vein injuries in C57BL/6 mice injected with FITC labelled fibrinogen and 80 nM (final concentration in mouse blood, equivalent to a dose of approximately 1.2 mg/Kg) anti-exosite 1 IgA (100 μl in PBS), and a region outside of injury site for comparison.

Figure 12:
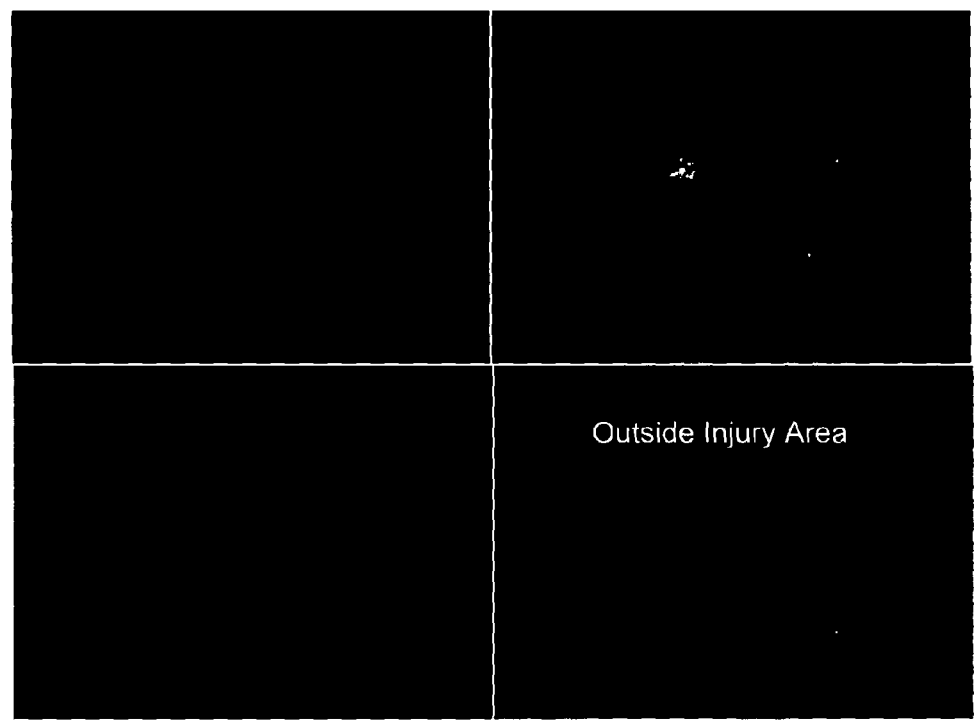

FIG. 12 shows fluorescence microscopy) images of $FeCl_3$ induced blood clots in femoral vein injuries in C57BL/6 mice injected with FITC labelled fibrinogen and 200 nM (final concentration in mouse blood, equivalent to a dose of approximately 3 mg/Kg) anti-exosite 1 IgA (100 μl in PBS), and a region outside of injury site for comparison.

Figure 13:
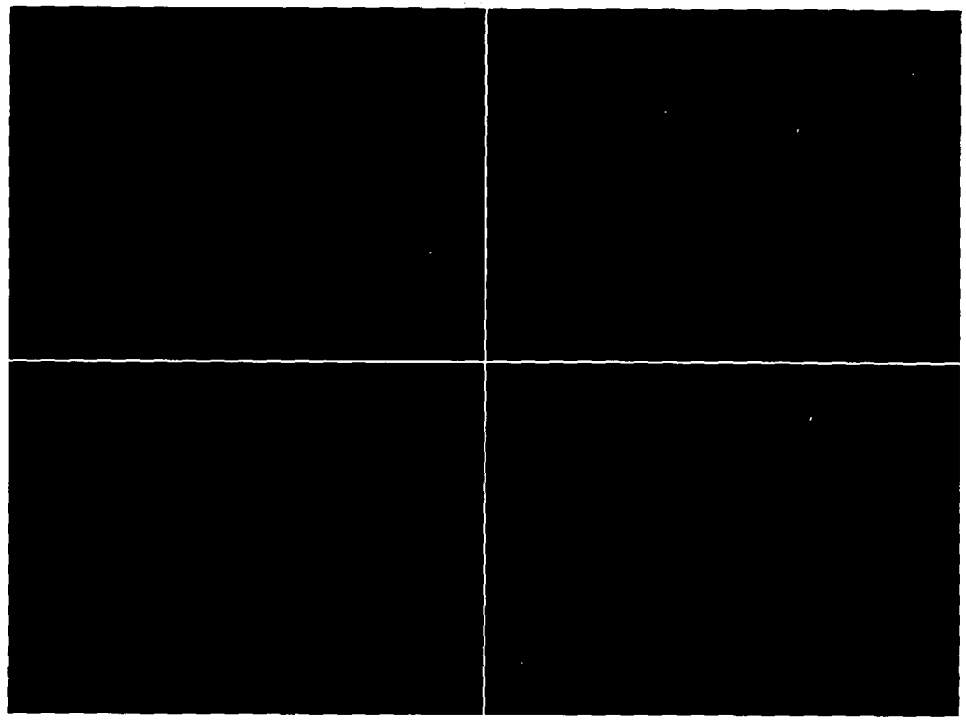

FIG. 13 shows fluorescence microscopy images of $FeCl_3$ induced blood clots in femoral vein injuries in C57BL/6 mice injected with FITC labelled fibrinogen and 400 nM (final concentration in mouse blood, equivalent to a dose of approximately 6 mg/Kg) anti-exosite 1 IgA (100 μl in PBS).

Figure 14:
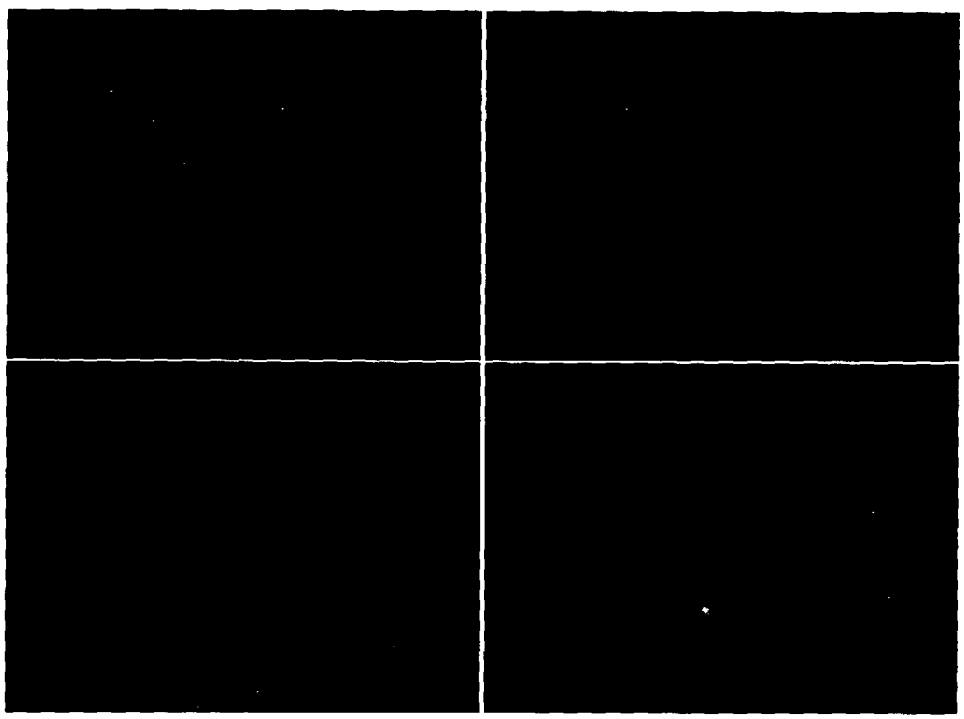

FIG. 14 shows fluorescence microscopy) images of $FeCl_3$ induced blood clots in femoral vein injuries in C57BL/6 mice treated with FITC labelled fibrinogen and 4 μM (final concentration in mouse blood, equivalent to a dose of approximately 60 mg/Kg) anti-exosite 1 IgA (100 μl in PBS).

Figure 15:
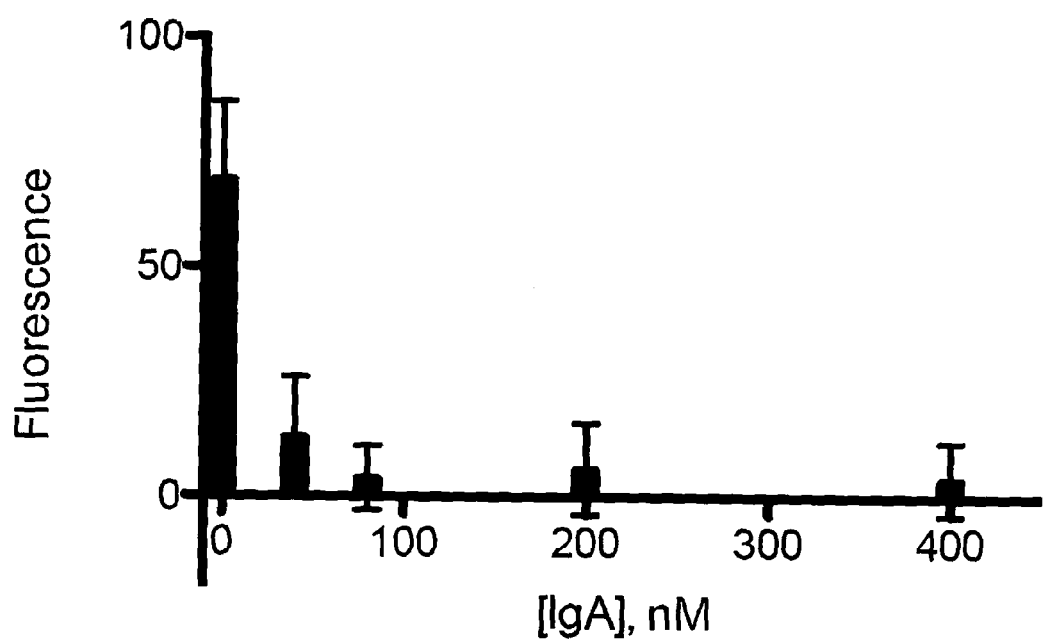

FIG. 15 shows a quantitation of the dose response to anti-exosite 1 IgA from the fluorescent images shown in FIGS. 9 to 13.

Figure 16:
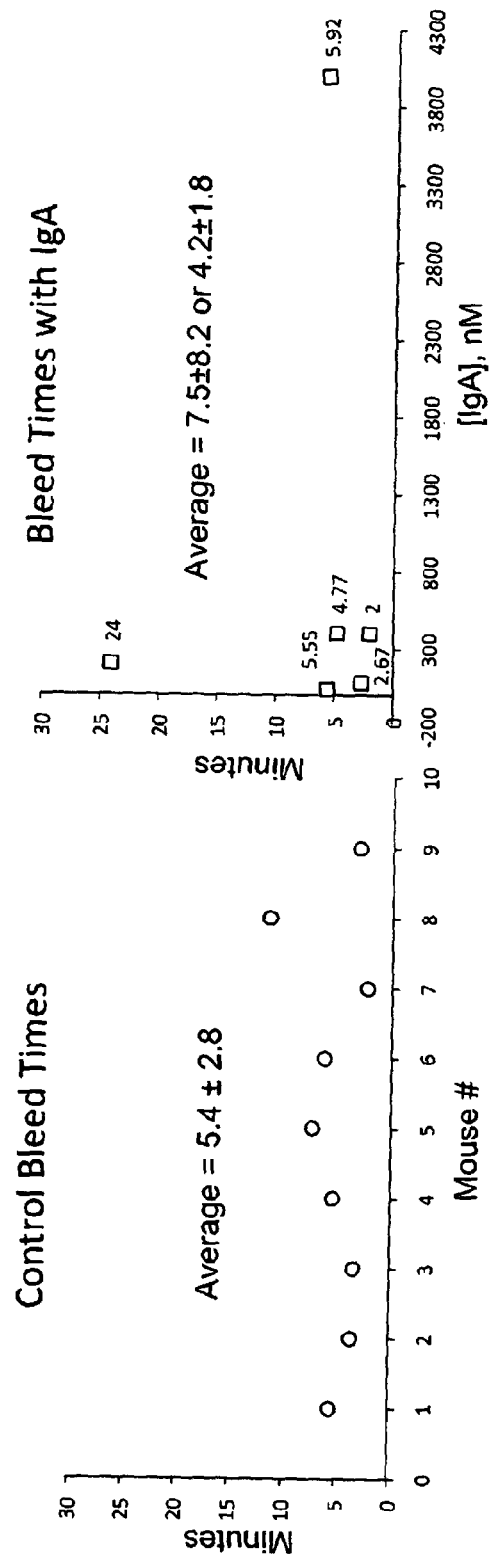

FIG. 16 shows tail bleed times in control C57BL/6 mice and in mice treated with increasing amounts of anti-exosite 1 IgA. The second average excludes the outlier.

Figure 17:
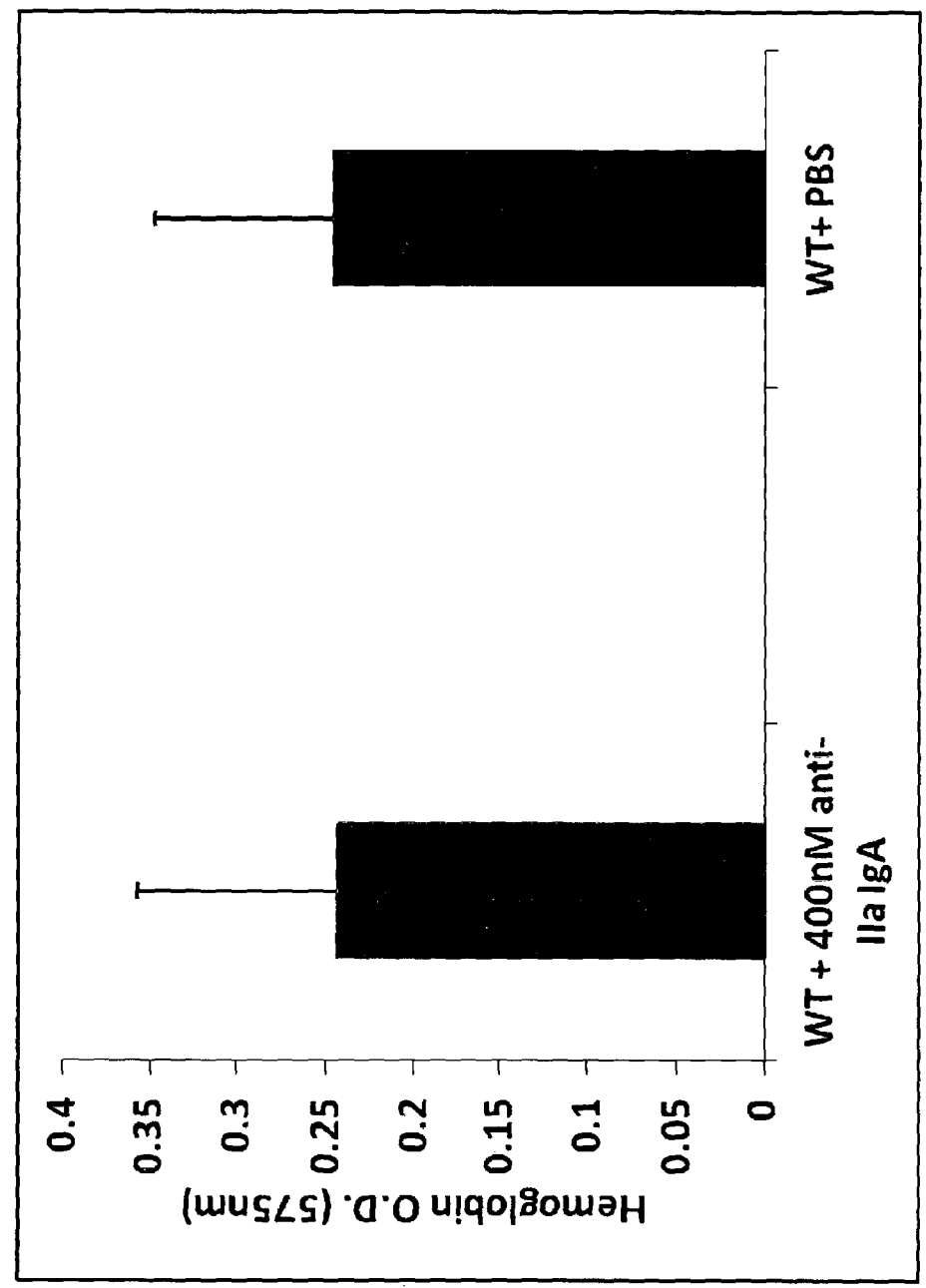

FIG. 17 shows the results of tail clip assays on wild-type male C57BL/6 mice (n=5) after injection into tail vein with either IgA or PBS. 15 mins after injection, tails were cut at diameter of 3 mm and blood loss monitored over 10 min.

Figure 18A:
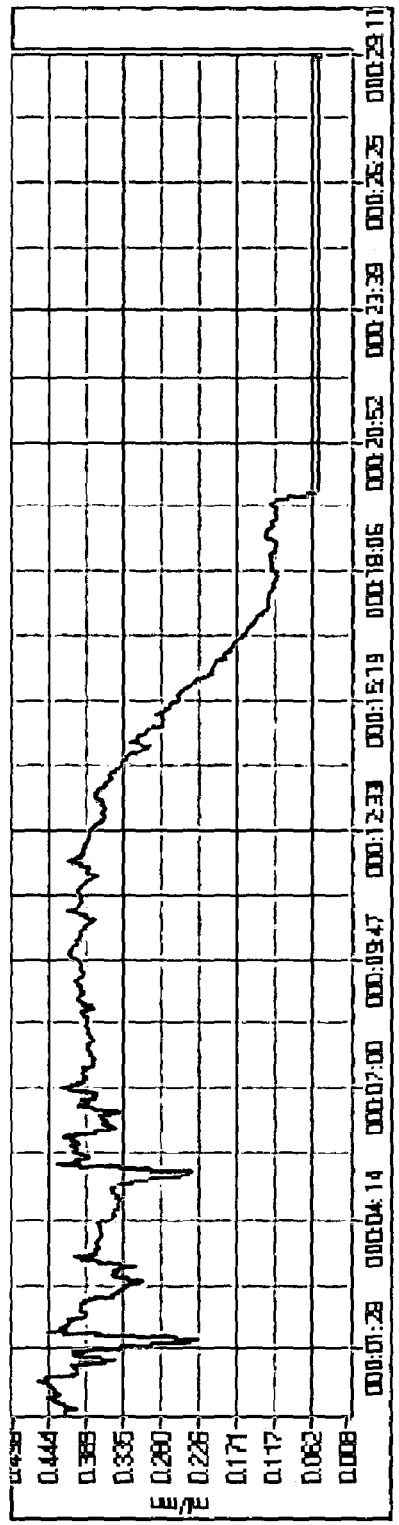
Figure 18B:
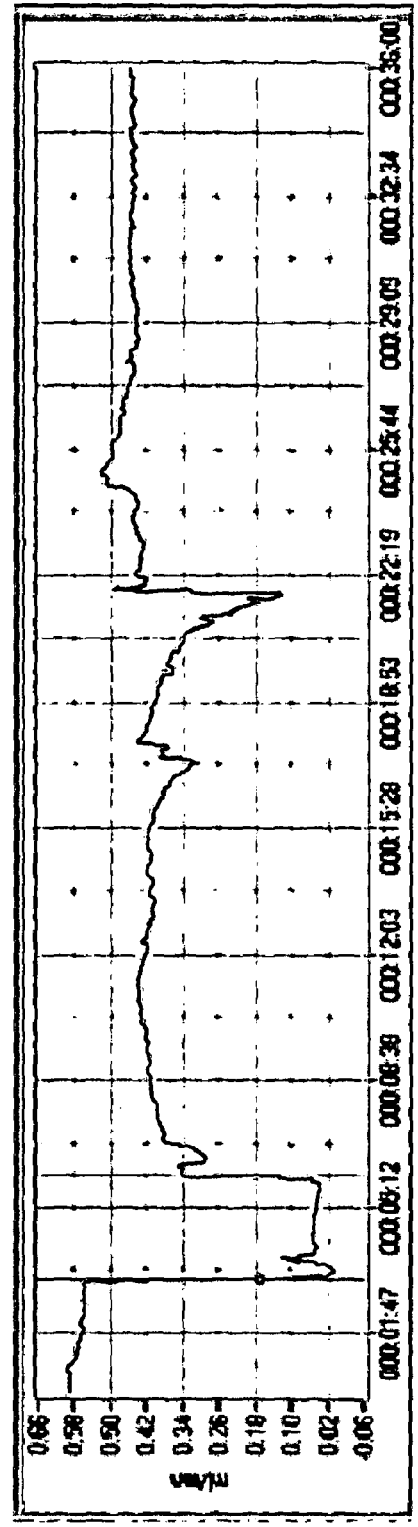
Figure 18C:
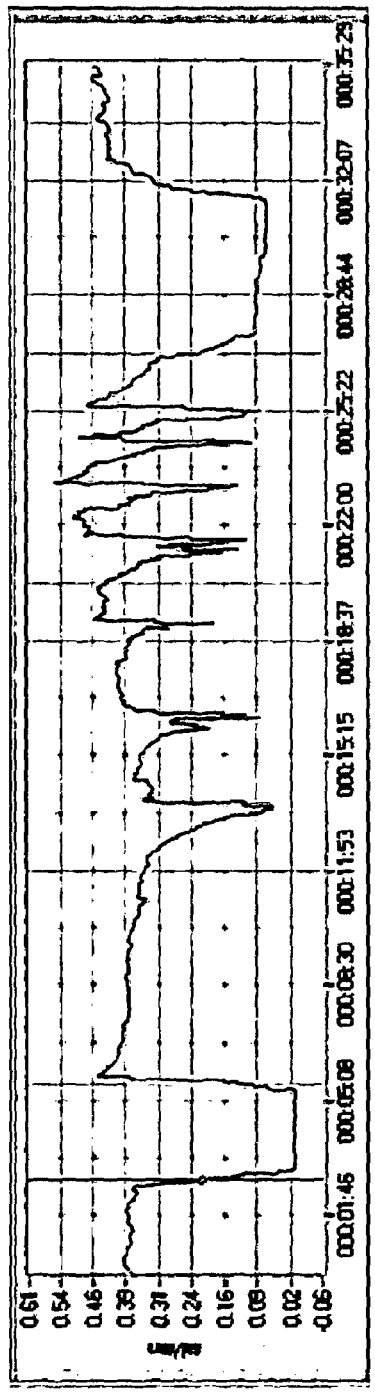
Figure 18D:
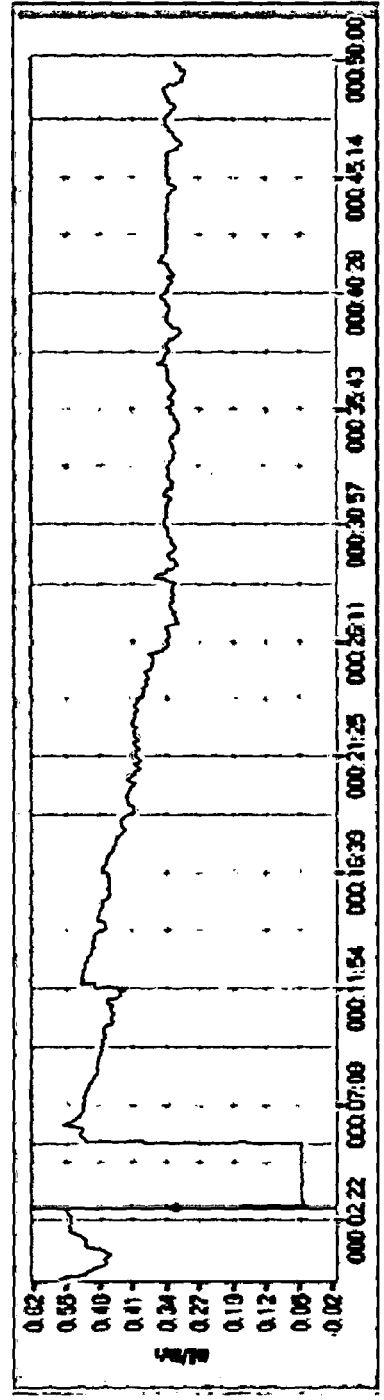

FIG. 18A to 18D show the results of an $FeCl_3$ carotid artery occlusion model on 9 week old WT C57BL/6 male mice injected as previously with 400 nM anti-thrombin IgA (final concentration in blood, equivalent to a dose of approximately 6 mg/Kg) or PBS 15 min prior to injury with 5% $FeCl_3$ for 2 min. FIG. 18A shows results for a typical PBS-injected mice (occlusion in 20 min) and FIGS. 18B, 18C and 18D show examples of results for mice treated with 400 nM anti-thrombin IgA (no occlusion).

Figure 19:
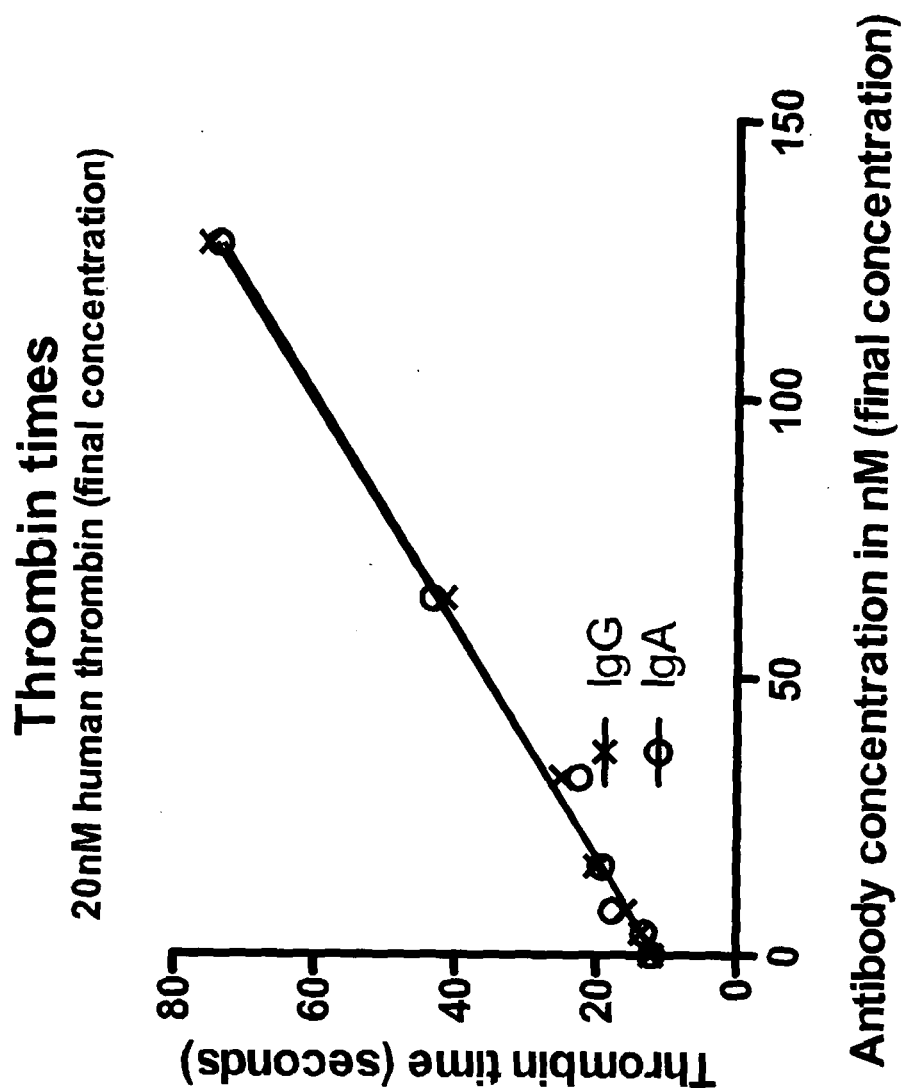

FIG. 19 shows thrombin times (i.e. clotting of pooled plasma) with increasing concentrations of IgG and IgA of the invention, upon addition of 20 nM human thrombin.

Figure 20:
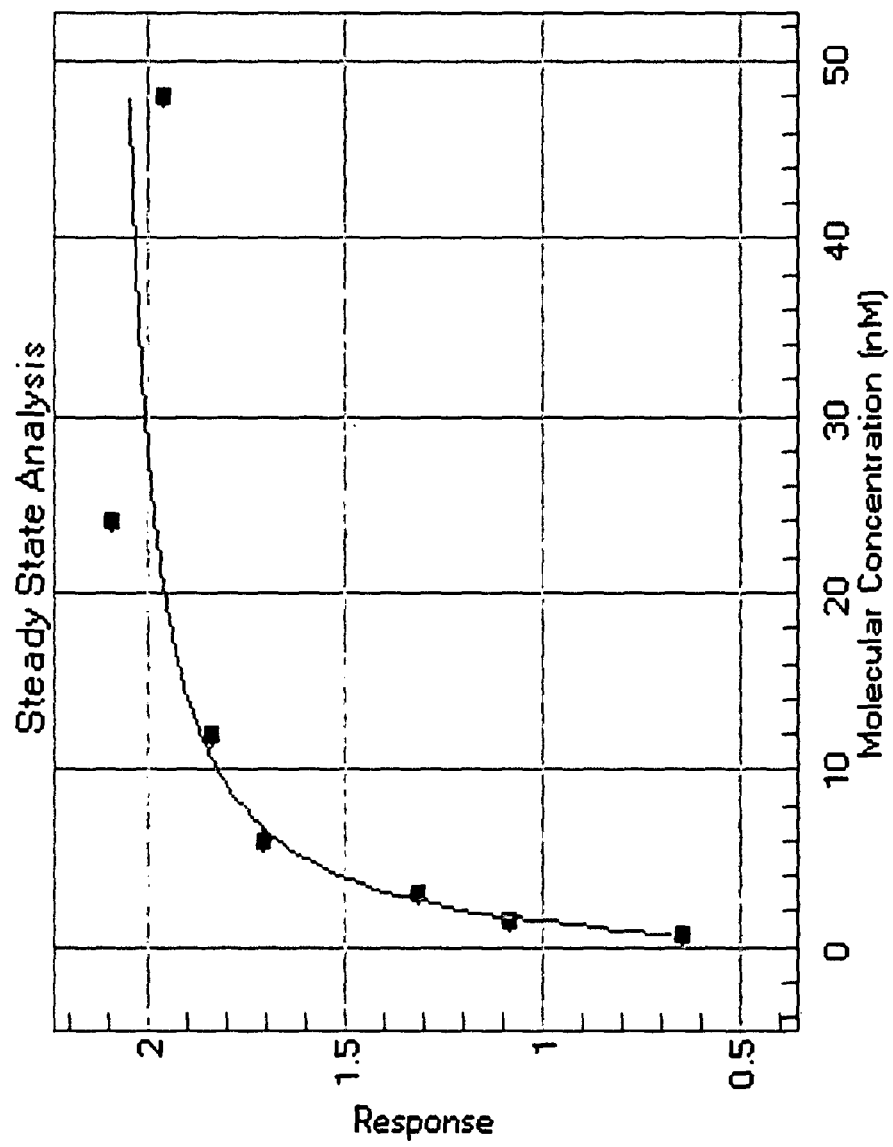

FIG. 20 shows the binding of synthetic IgG to immobilized thrombin (on ForteBio Octet Red instrument).

Figure 21:
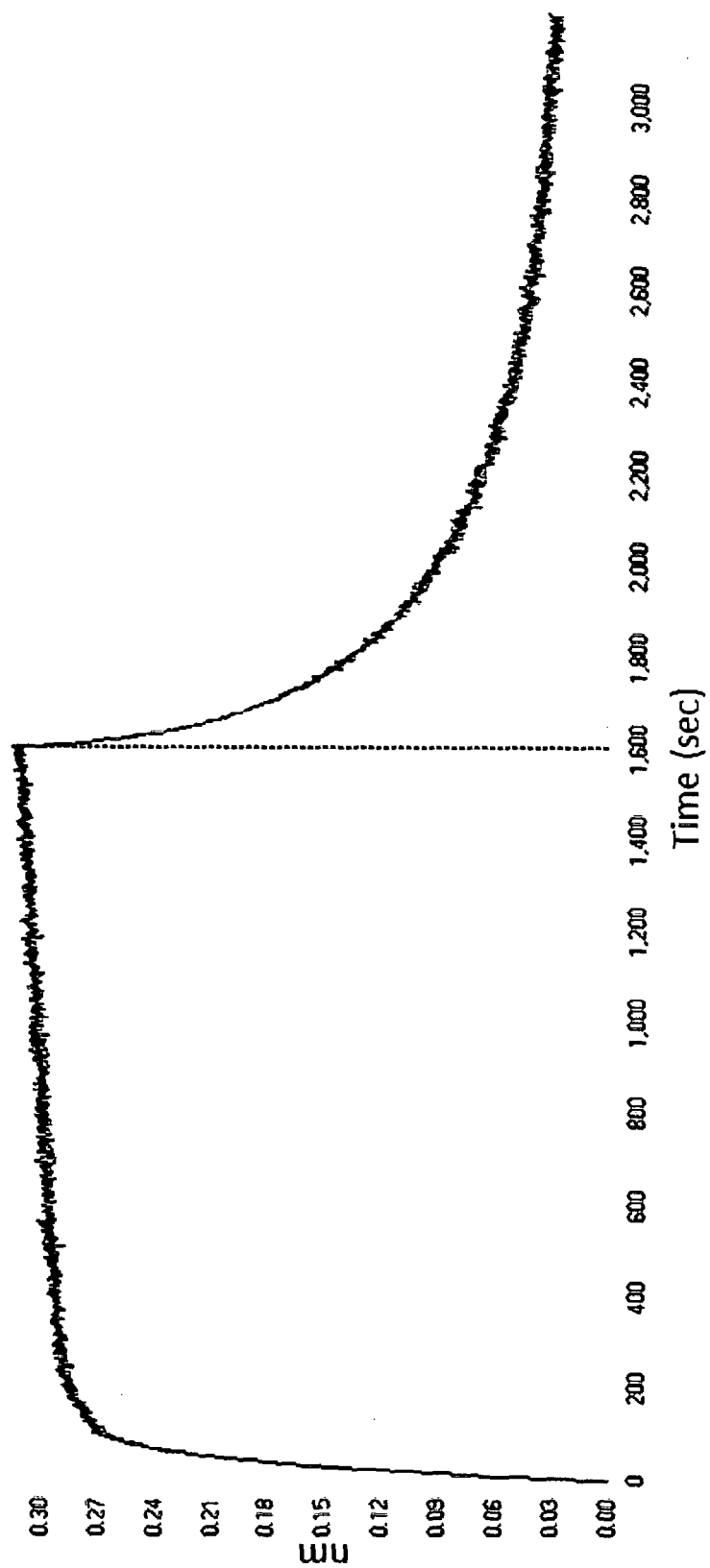

FIG. 21 shows a typical Octet trace for the binding of 24 nM S195A thrombin to immobilized IgG showing the on phase, followed by an off phase. The black line is the fit.

Figure 22:
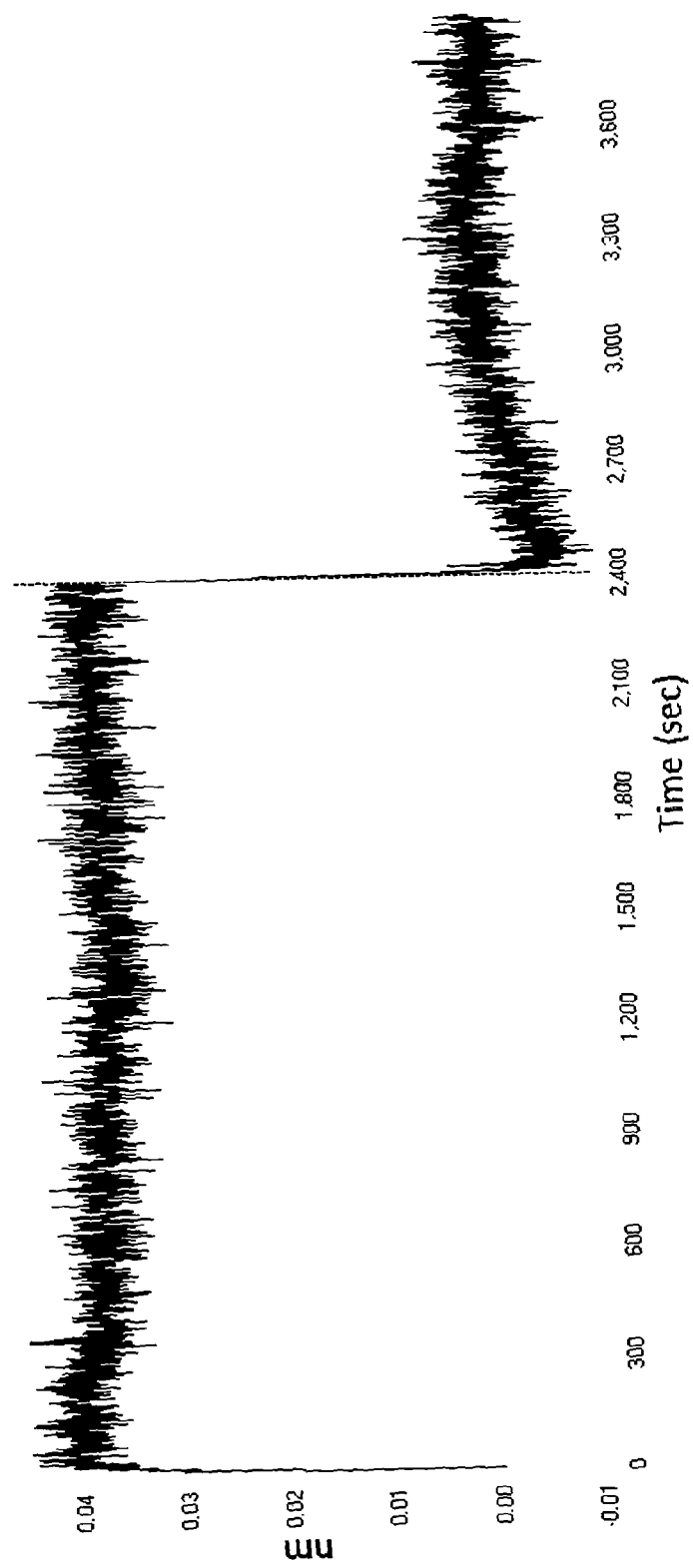

FIG. 22 shows an Octet trace of 500 nM prothrombin with a tip loaded with immobilized IgG. The same conditions were used as the experiment with thrombin in FIG. 21. There is no evidence of binding, even at this high concentration.

EXPERIMENTS

1. Antibody Isolation and Characterisation

Coagulation screening was carried out on a blood plasma sample from a patient. The coagulation tests were performed on a patient who suffered subdural haematoma following head injury. The haematoma spontaneously resolved without intervention. There was no previous history of bleeding and in the 4 years since the patient presented, there have been no further bleeding episodes. The results are shown in Table 1.

The prothrombin time (PT), activated partial thromboplastin time (APTT), and thrombin time (TT) were all prolonged in the patient compared to controls, but reptilase time was normal.

Thrombin time was not corrected by heparinase, indicating that heparin treatment or contamination was not responsible. Fibrinogen levels were normal in the patient, according to ELISA and Reptilase assays. The Clauss assay gave an artifactally low fibrinogen level due to the presence of the thrombin inhibitor. The PT and APTT clotting times were found to remain prolonged following a mixing test using a 50:50 mix with pooled plasma from normal individuals. This showed the presence of an inhibitor in the sample from the patient.

Figure 1:
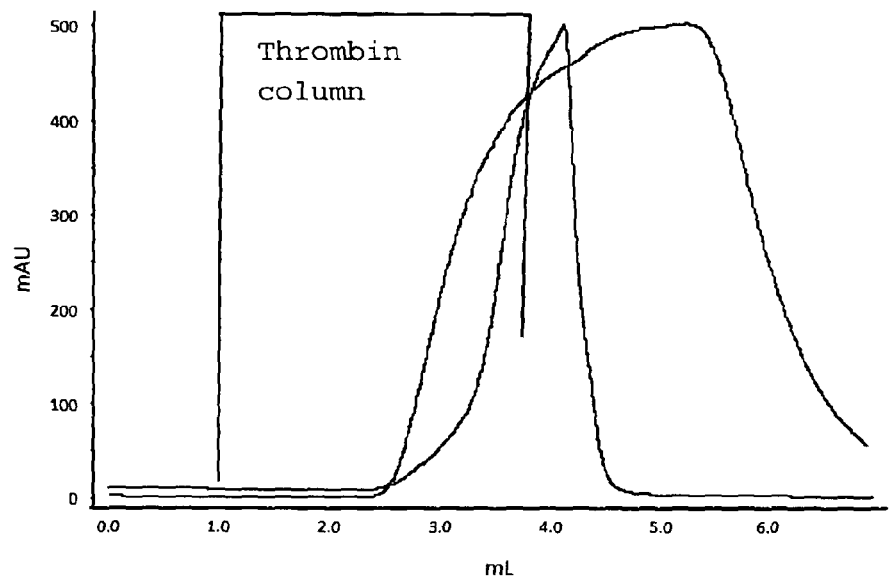
Figure 1:
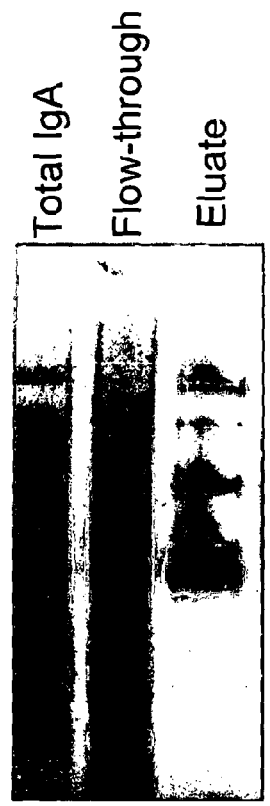
Figure 2:
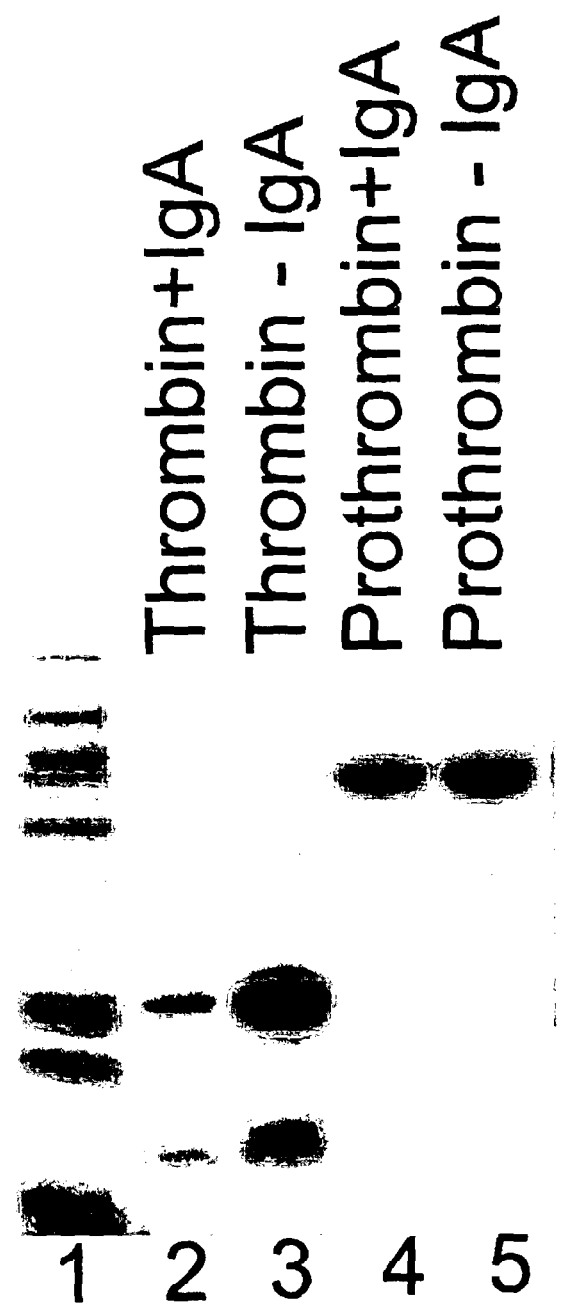

The patient's blood plasma was found to have a high titre of an IgA. This IgA molecule was found to bind to a human thrombin column (FIG. 1). IgA binding lectin-agarose pulled down thrombin in the presence but not the absence of the IgA. Prothrombin was not pulled down by the lectin-agarose in the presence of the IgA, indicating that the IgA specifically binds to thrombin but not prothrombin (FIG. 2).

The binding site of the IgA on the thrombin molecule was then investigated.

Figure 3:
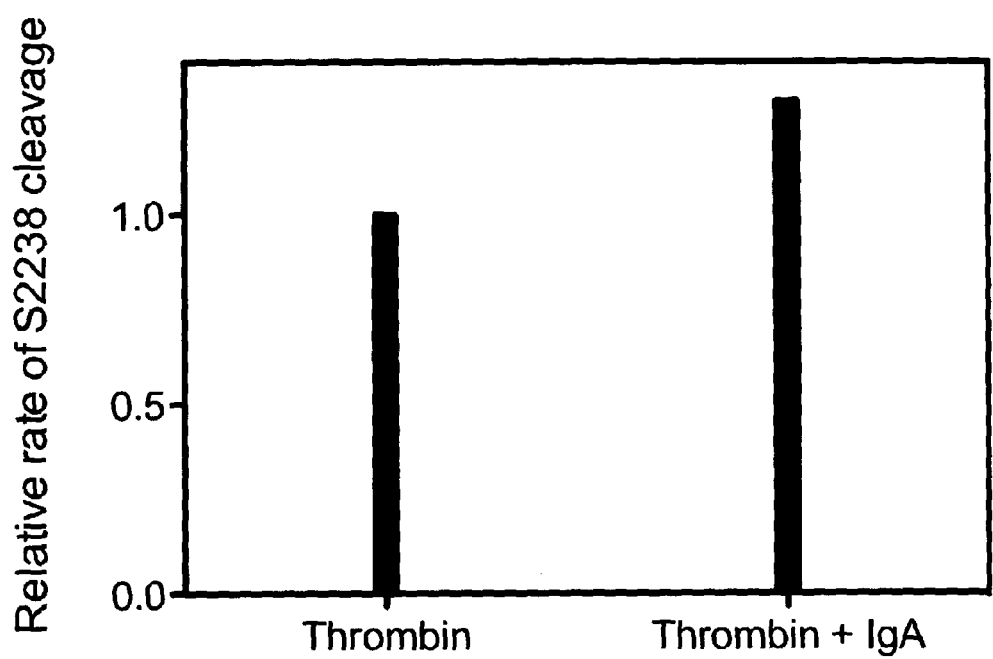
FIG. 3 shows the relative rate of S2238 cleavage by thrombin in the presence or absence of IgA (i.e. a single slope of Abs405 with time for S2238 hydrolysis). This indicates that the IgA does not bind at the thrombin active site.

A slightly higher rate of cleavage of S2238 by thrombin was measured in the presence of the IgA, indicating that the IgA does not block the active site of thrombin (FIG. 3).

Figure 4:
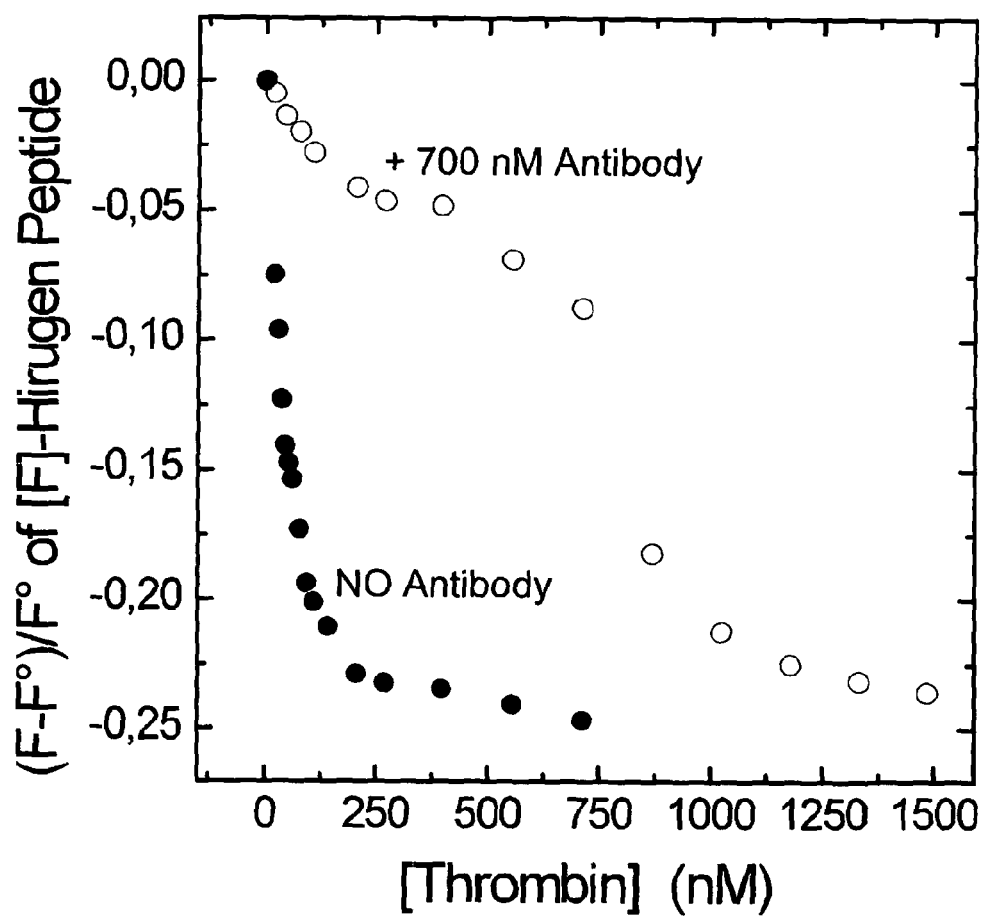
FIG. 4 shows the results of binding studies which indicate that the IgA competes with the fluorescently labelled dodecapeptide hirugen for binding to thrombin.

The binding of fluorescently labelled hirugen to thrombin is inhibited by the presence of 700 nM of the IgA, indicating that the epitope for the antibody overlaps with the binding site of hirugen on thrombin, namely the exosite 1 of thrombin (FIG. 4).

The effect of the IgA on the hydrolysis of some of thrombin's procoagulant substrates was tested. The results are shown in Table 2. These results demonstrate that the IgA molecule isolated from the patient sample inhibits multiple procoagulant activities of thrombin.

Inhibition of thrombin by antithrombin (AT) in the presence of the IgA was only marginally affected in both the absence and presence of heparin (Table 3).

Figure 5:
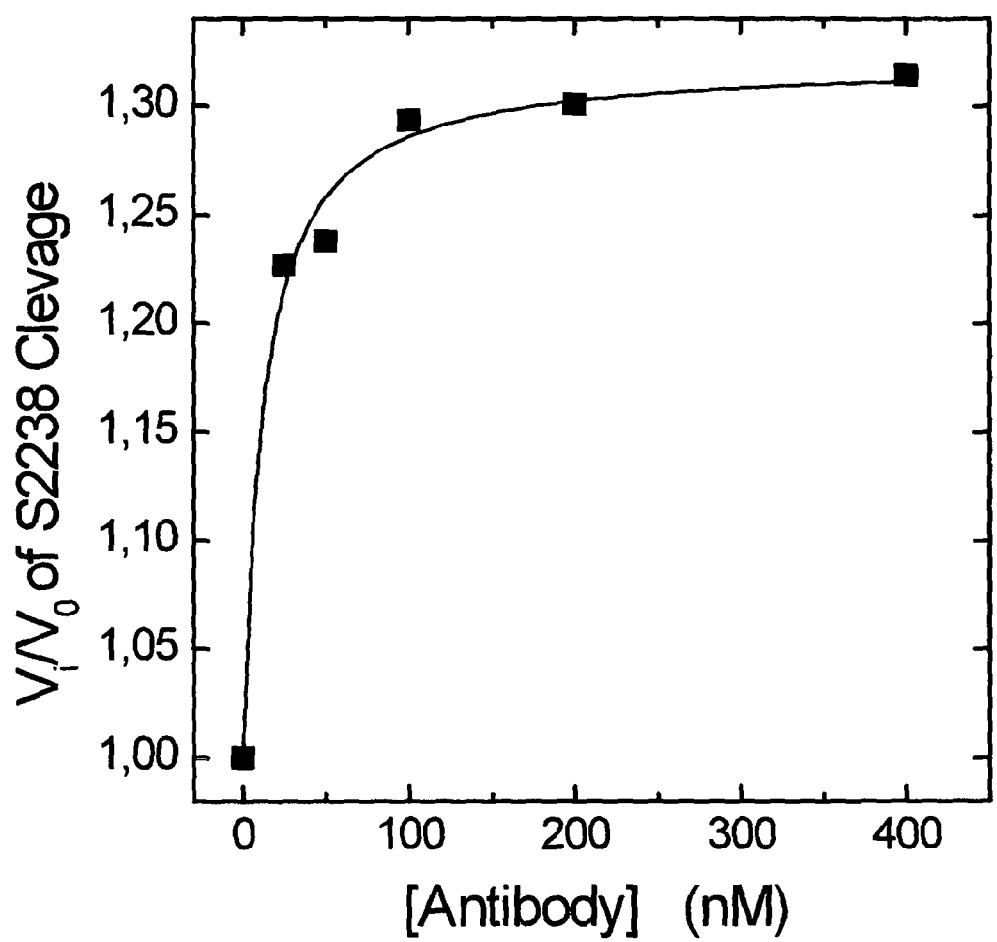
FIG. 5 shows the effect of the IgA on the cleavage of S2238 by thrombin. This analysis allows the estimate of Kd for the IgA-thrombin interaction of 12 nM.

The dissociation constant ($K_d$) of the IgA for thrombin was initially estimated based on rate of S2238 hydrolysis to be approximately 12 nM (FIG. 5). The $K_d$ for the binding of the IgA to S195A thrombin (inactivated by mutation of the catalytic serine) was determined to be 2 nM using the ForteBio Octet Red instrument (Table 4).

Figure 6:
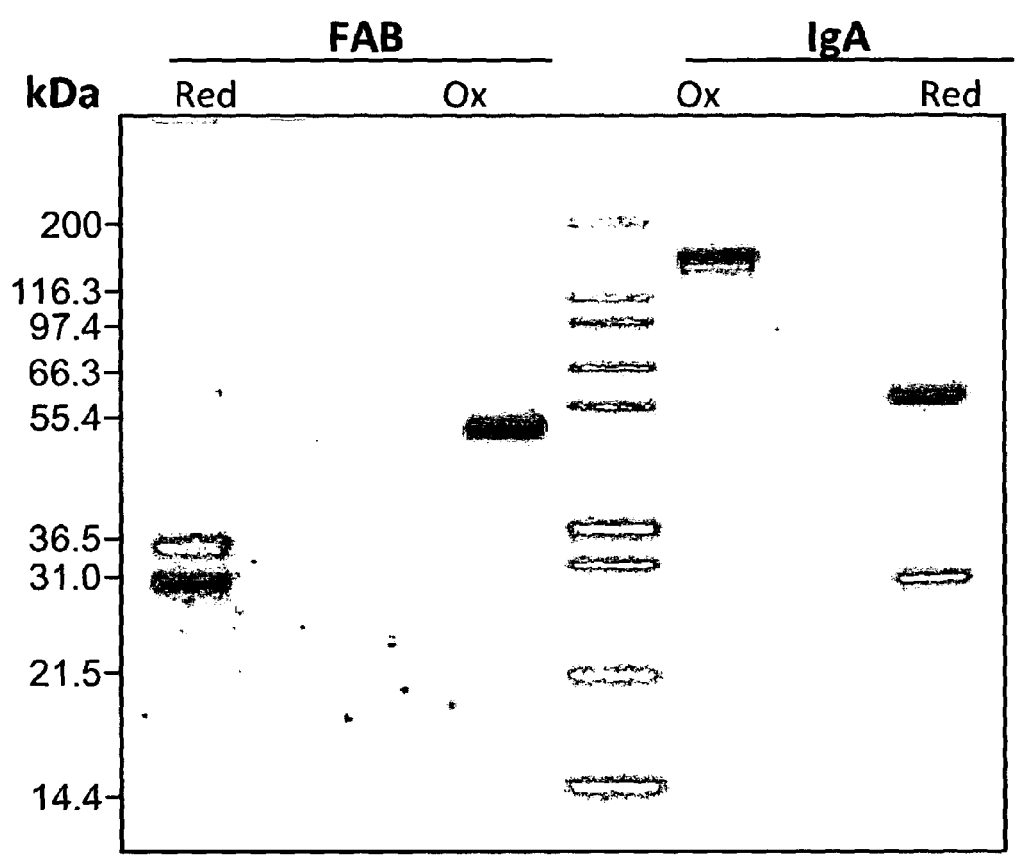
FIG. 6 shows an SDS-PAGE gel of whole IgA and Fab fragments under reducing and non-reducing (ox) conditions. The non-reduced IgA is shown to have a molecular weight of between 100-200 kDa and the non-reduced Fab has a molecular weight of about 50 kDa.
Figure 7:
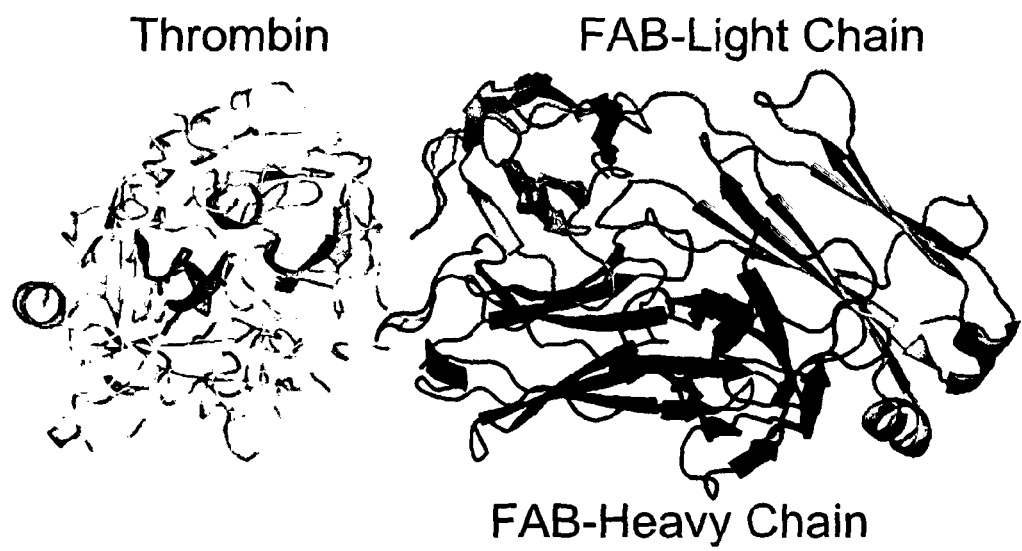
FIG. 7 shows the crystal structure of Thrombin-Fab complex showing interaction between the exosite 1 of thrombin and HCDR3 of the Fab fragment.

The purified IgA was cleaved with papain (FIG. 6), and the Fab fragment was isolated and combined with human PPACK-Thrombin (PPACK is a covalent active site inhibitor). The human PPACK-Thrombin-FAB complex was crystallized and used for structural analysis. The statistics of the structure obtained were as follows: resolution is 1.9 Å; Rfactor=19.43%; Rfree=23.42%; one complex in the asymmetric unit; Ramachandran: favoured=97.0%, outliers=0%. The crystal structure revealed a close association between the HCDR3 of the IgA Fab and the exosite 1 of thrombin (FIG. 7).

Figure 8:
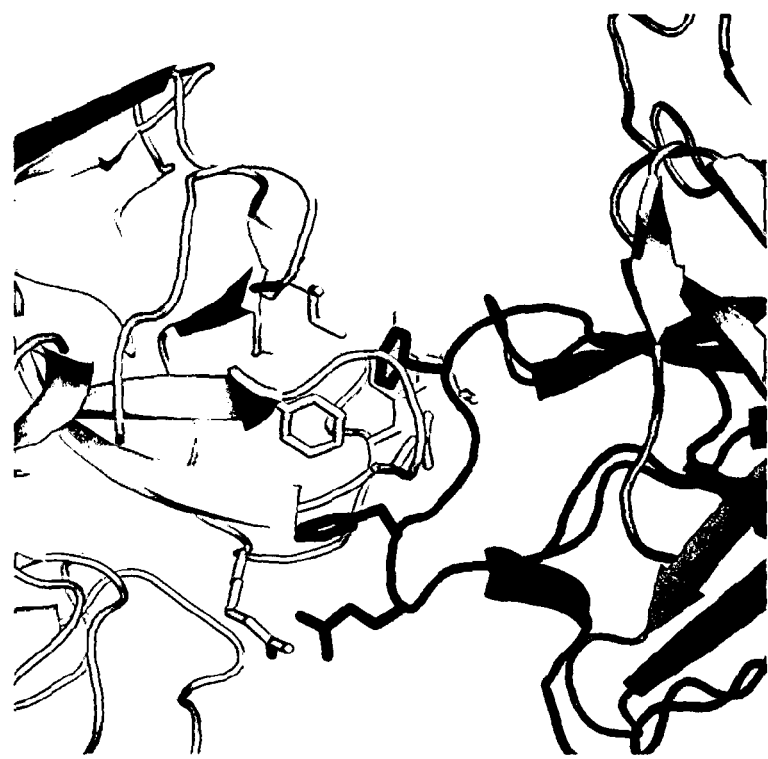
FIG. 8 shows detail of crystal structure showing interaction between specific residues of thrombin exosite 1 and HCDR3 of the Fab fragment.

In particular, residues M32, F34, Q38, E39, L40, L65, R67, R73, T74, R75, Y76, R77a and I82 of the exosite 1 all directly interact with the HCDR3 loop of the IgA Fab (FIG. 8).

PISA analysis of the antibody-thrombin interface showed that the total buried surface area in the complex is 1075 Å$^2$. The contact residues in the IgA heavy chain were (Kabat numbering): 30, 51, 52a, 53-55, 96, 98, 99, 100, 100a, 100b, 100c, 100d). These are all in CDRs: CDRH1—GYTL TEAAIH; CDRH2—GLDPQDGETVYAQQFKG; CDRH3—GDFSEFEPFSMDYFHF (underlined residues contacting). CDRH3 was found to be the most important, providing 85% of the buried surface area on the antibody. The light chain made one marginal contact with Tyr49, right before CDRL2 (with Ser36a of thrombin). Some individual contributions to buried surface were: Glu99 54 Å$^2$, Phe100 134.8 Å$^2$, Glu100Ca 80.6 Å$^2$, Phe100c 141.7 Å$^2$.

The contact residues in thrombin were found to be (chymotrypsin numbering): 32, 34, 36a-40, 65, 67, 73-76, 77a, 82, and 151. The most important individual contributors to the buried surface were: Gln38 86.4 Å$^2$, Arg73 44.5 Å$^2$, Thr74 60.1 Å$^2$, Tyr76 78.4 Å$^2$, Arg77a 86.9 Å$^2$.

The patient did not display increased or abnormal bleeding or haemorrhage, in spite of 3 g/l circulating levels of this IgA, demonstrating that the antibody inhibits thrombin without affecting normal haemostasis.

2. The Effect of IgA on Animal Thrombosis Models

C57BL/6 mice were anaesthetized. A catheter was inserted in the carotid artery (for compound injection). FITC labelled fibrinogen (2 mg/ml) was injected via the carotid artery. PBS (control) or IgA was also injected via the carotid artery. The femoral vein was exposed and 10% FeCl$_3$ applied (saturated blotting paper 3 mm in length) for 3 min to induce clotting.

Fluorescence microscopy images were taken along the length of injury site at 0, 5, 10, and 20 min post FeCl$_3$ injury using fluorescence microscopy techniques.

Figure 9:
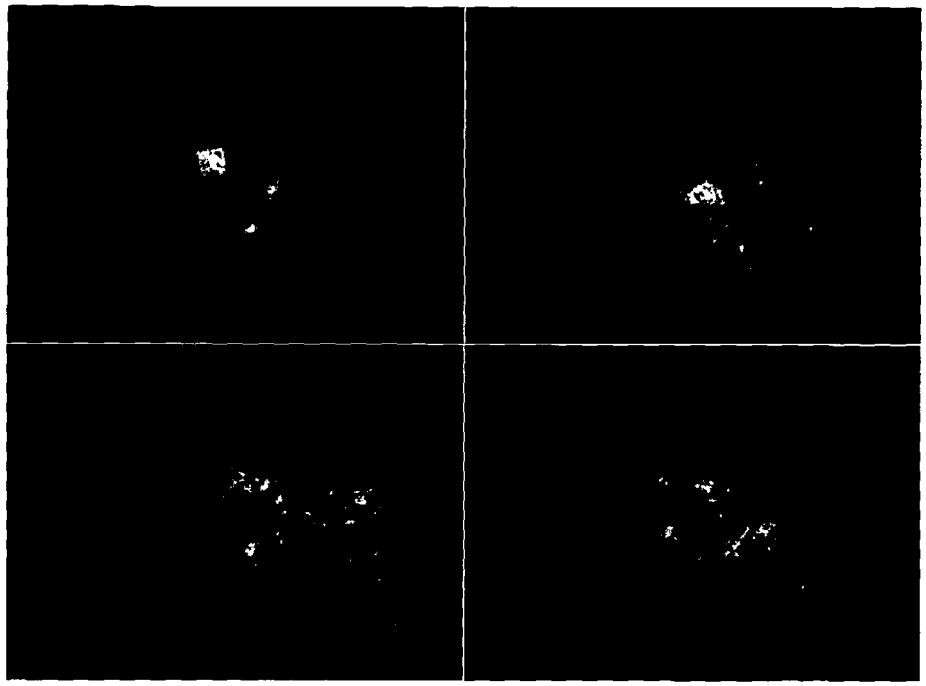
FIG. 9 shows fluorescence microscopy images of $FeCl_3$ induced blood clots in femoral vein injuries in C57BL/6 mice injected with FITC labelled fibrinogen taken at between 2 and 30 minutes. 100 ul of PBS was administered (vehicle control).

Clots (fibrin deposits) in the femoral vein were clearly visible as bright areas (FIG. 9). The lowest dose of the antibody was observed to cause significant inhibition of clotting but as the dose increased, clotting was abolished (FIGS. 10 to 15).

The bleeding times of the mice were also measured. Bleeding times were assessed as time to cessation of blood flow after a tail cut. Despite the presence of a single outlier sample, the bleeding time was found to be unaffected by treatment with anti-exosite 1 IgA (FIG. 16).

These results show that the anti-exosite 1 IgA antibody is a potent inhibitor of thrombosis but has no effect on bleeding time.

3. Tail Clip Assays

A tail clip assay was performed on wild-type male C57BL/6 mice injected with either 400 nM IgA (final concentration in blood, equivalent to a dose of approximately 6 mg/Kg) or PBS. Blood loss was monitored over 10 mins after the tail was cut at 3 mm diameter 15 minutes after the injection. Total blood loss was found to be unaffected by treatment with anti-exosite 1 IgA (FIG. 17).

4. FeCl$_3$ Injury Carotid Artery Occlusion

FeCl$_3$ injury carotid artery occlusion studies were performed on 9 week old WT C57BL/6 male mice. Mice were injected with 400 nM anti-IIa IgA (final concentration in blood, equivalent to a dose of approximately 6 mg/Kg) or PBS 15 min prior to injury with 5% FeCl$_3$ for 2 min. Blood flow was then monitored by Doppler and the time to occlusion measured. A "clot" was defined as stable occlusive thrombus where blood flow was reduced to values typically less than 0.1 ml/min and stayed reduced. In the control mice, a stable clot was observed to form about 20 mins after injury (FIG. 18A). However, the majority of mice treated with 400 nM anti-IIa IgA were unable to form stable clots and gave traces in which the clots were quickly resolved, repeatedly resolved or never formed. Three representative traces are shown in FIGS. 18B to 18D.

5. Anti-Exosite 1 IgG

The IgA molecule identified in the patient described above was re-formatted as an IgG using standard techniques.

The clotting time of pooled human plasma spiked with increasing amounts of the original IgA and the new IgG was tested upon addition of human thrombin to 20 nM (FIG. 19). Both parent IgA and the synthetic IgG increased time to clot formation in an identical concentration-dependent manner, implying identical affinities for thrombin.

This was confirmed by measuring the binding of synthetic IgG to immobilized S195A thrombin using a ForteBio™ Octet Red instrument. Thrombin was attached to the probe and the binding of the antibodies (at various concentrations) was monitored. On-rates and off-rates were determined. Both antibodies gave similar on-rates of approximately $3\times10^5$ M$^{-1}$s$^{-1}$ and off-rates of approximately $5\times10^{-4}$ s$^{-1}$, and dissociation constants (Kd) of approximately 2 nM. Kds of approximately 2 nM were also obtained for the IgA and the IgG by steady-state analysis (Table 4). A representative steady state curve is shown in FIG. 20. The properties of the IgA were therefore reproduced on an IgG framework.

Binding of prothrombin to the IgG antibody was tested using the Octet system by immobilizing IgG. Thrombin bound to the immobilized IgG with comparable rates and affinities as those obtained using immobilized thrombin (Table 4); prothrombin did not bind to the IgG. FIG. 21 is a trace of 24 nM thrombin binding to and dissociating from the immobilized IgG. FIG. 22 is the same experiment using 500 nM prothrombin, and shows no evidence of binding.

| Sequences |
|---|

Amino acid sequence of human preprothrombin (SEQ ID NO: 1; GeneID: 2147; NP_000497.1 GI: 4503635; exosite 1 residues underlined)

```
  1 mahvrglqlp gclalaalcs lvhsqhvfla pqqarsllqr vrrantflee vrkgnlerec
 61 veetcsyeea fealesstat dvfwakytac etartprdkl aaclegncae glgtnyrghv
121 nitrsgiecq lwrsryphkp einstthpga dlgenfornp dssttgpwcy ttdptvrrqe
181 csipvcgqdq vtvamtprse gssvnlsppl eqcvpdrgqq yqgrlavtth glpclawasa
241 qakalslkhqd fnsavqlven fcrnpdgdee gvwcyvagkp gdfgycdlny ceeaveeetg
301 dgldedsdra iegrtatsey qtffnprtfg sgeadcglrp lfekksledk terellesyl
361 dgrivegsda eigmspwqvm lfrkspqell cgaslisdrw vltaahclly ppwdknften
421 dllvrigkhs rtryerniek ismleklyih prynwrenld rdialmklkk pvafsdyihp
481 vclpdretaa sllqagykgr vtgwgnlket wtanvgkqqp svlqvvnlpi verpvckdst
541 riritdnmfc agykpdegkr gdacegdsgg pfvmkspfnn rwyqmgivsw gegcdrdgky
601 gfythvfrlk kwiqkvidqf ge
```

Amino acid sequence of anti-exosite 1 IgA and IgG VH domain with Kabat Numbering (CDRs underlined):

(SEQ ID NO: 2)
```
QVQLIQSGSAVKKPGASVRVSCKVSGYILTEAAIHWVRQAPGKGLEWMGG
         10        20        30        40        50

LDPQDGETVYAQQFKGRVTMTEDRSTDTAYMEVNNLRSEDTATYYCTTGD
52a       60        70        8082abc      90

FSEFEPFSMDYFHFWGQGTVVTVAS.
 100abcdefgh      110
```

Amino acid sequence of anti-exosite 1 IgA and IgG HCDR1
(SEQ ID NO: 3)
GYTLTEAAIH.

Amino acid sequence of anti-exosite 1 IgA and IgG HCDR2
(SEQ ID NO: 4)
GLDPQDGETVYAQQFKG.

Amino acid sequence of anti-exosite 1 IgA and IgG HCDR3
(SEQ ID NO: 5)
GDFSEFEPFSMDYFHF.

Amino acid sequence of anti-exosite 1 IgA and IgG VL domain with Kabat Numbering:
(SEQ ID NO: 6)
```
EIVLTQSPATLSLSPGERATLSCRASQNVSSFLAWYQHKPGQAPRLLIYD
         10        20        30        40        50

ASSRATDIPIRFSGSGSGTDFTLTISGLEPEDFAVYYCQQRRSWPPLTFG
         60        70        80        90   95a

GGTKVEIKR.
 100     108
```

Amino acid sequence of anti-exosite 1 IgA and IgG LCDR1
(SEQ ID NO: 7)
RASQNVSSFLA.

Amino acid sequence of anti-exosite 1 IgA and IgG LCDR2
(SEQ ID NO: 8)
DASSRAT.

Amino acid sequence of anti-exosite 1 IgA and IgG LCDR3
(SEQ ID NO: 9)
QQRRSWPPLT.

TABLE 1

Coagulation Screening Results

| Test | | Result | Control/Normalised Ratio (NR) |
|---|---|---|---|
| Prothrombin Time | | 43 sec. | NR = 11-13 sec. |
| | 50:50 correction | 35 sec. | |
| Act. part. Thromboplastin Time | | 157 sec. | NR = 22-23 sec. |
| | 50:50 correction | 105 sec. | |
| Thrombin Time | | >150 sec. | NR = 10-13 sec. |
| Reptilase Time | | 16 sec. | Control = 15 sec. |
| Fibrinogen | Clauss | 0.7 g/l | NR = 1.5-4.5 g/l |
| | Antigenic | 5.0 g/l | |

TABLE 2

Effect of anti-exosite 1 IgA on thrombin hydrolysis of procoagulant substrates

| Thrombin substrate | Activity | Antibody Effect |
|---|---|---|
| Fibrinogen | Formation of fibrin clot | No detectable cleavage |
| Platelet receptor PAR-1 peptide | Activation of platelets | 15-fold decrease in hydrolysis |
| FVIII | Feedback activation of thrombin via Xase complex | 7-fold decrease in hydrolysis |

TABLE 3

Effect of saturating concentration of anti-exosite 1 IgA (Fab) on thrombin inhibition by antithrombin (AT) in the absence and presence of 1 nM heparin (Hep).

| | Rate of Inhibition ($M^{-1}s^{-1}$) | Heparin effect |
|---|---|---|
| AT | $4.8 \pm 0.2 \times 10^3$ | 2.4-fold |
| AT + Hep | $11.8 \pm 0.3 \times 10^3$ | |
| AT + Fab | $1.7 \pm 0.1 \times 10^3$ | 3.3-fold |
| AT + Hep + Fab | $5.6 \pm 0.3 \times 10^3$ | |

TABLE 4

Binding constants of anti-exosite 1 IgA (n = 1 under this precise condition), IgG (n = 3) antibodies, and IgG-derived FAB to S195A thrombin (active site free, recombinant thrombin).

| | Kd (nM)* | $k_{on}$ ($M^{-1}s^{-1}$) | $k_{off}$ ($s^{-1}$) | Kd (nM)# |
|---|---|---|---|---|
| IgA | 1.8 | $3.3 \times 10^5$ | $3.7 \times 10^{-4}$ | 1.2 |
| IgG | $1.5 \pm 0.3$ | $3.3 \pm 0.5 \times 10^5$ | $6.8 \pm 1.1 \times 10^{-4}$ | $2.1 \pm 0.3$ |
| IgG FAB | ND | $5.0 \times 10^5$ | $2.7 \times 10^{-3}$ | 5.3 |
| IgG FAB⁺ | $3.3 \pm 0.3$ | $4.3 \times 10^5$ | $2.1 \times 10^{-3}$ | 4.9 |

*Kd determined from steady-state analysis of response vs. concentration.
Kd calculated from rates.
⁺Determined using immobilised FAB.

The invention claimed is:

1. A recombinant antibody molecule, comprising a VH domain having the amino acid sequence of SEQ ID NO: 2, a VL domain, and an IgG constant region, wherein the recombinant antibody molecule specifically binds to the exosite 1 region of thrombin.

2. An antibody molecule according to claim 1 that inhibits thrombin activity.

3. An antibody molecule according to claim 2, wherein the antibody does not inhibit hemostasis and does not cause bleeding in vivo.

4. An antibody molecule according to claim 1, wherein the VL domain comprises an LCDR1 having the amino acid sequence of SEQ ID NO: 7, an LCDR2 having the amino acid sequence of SEQ ID NO: 8, and an LCDR3 having the amino acid sequence of SEQ ID NO: 9.

5. An antibody molecule according to claim 1, wherein the VL domain has the amino acid sequence of SEQ ID NO: 6 or the amino acid sequence of SEQ ID NO: 6 with one or more amino acid substitutions.

6. An antibody molecule according to claim 4, wherein the VL domain has the amino acid sequence of SEQ ID NO: 6.

7. A recombinant antibody molecule, comprising a VH domain comprising
an HCDR3 having the amino acid sequence of SEQ ID NO: 5,
an HCDR2 having the amino acid sequence of SEQ ID NO: 4, and an HCDR1 having the amino acid sequence of SEQ ID NO: 3,
a VL domain comprising an LCDR1 having the amino acid sequence of SEQ ID NO: 7 or the amino acid sequence of SEQ ID NO: 7 with one or two amino acid substitutions, an LCDR2 having the amino acid sequence of SEQ ID NO: 8, and an LCDR3 having the amino acid sequence of SEQ ID NO: 9, and an IgG constant region, wherein the recombinant antibody molecule specifically binds to the exosite 1 region of thrombin.

8. An antibody molecule according to claim 1, wherein the antibody molecule is a monoclonal antibody.

9. An antibody molecule according to claim 1, wherein the antibody molecule is a minibody.

10. A pharmaceutical composition, comprising the antibody molecule according to claim 1 and a pharmaceutically acceptable carrier or excipient.

11. The antibody molecule according to claim 1, wherein the IgG constant region is an IgG1 or IgG4 constant region.

12. The antibody molecule according to claim 1, wherein the antibody molecule is a human antibody.

13. The antibody molecule according to claim 5, wherein the VL comprise an amino acid substitution at Asn28 of SEQ ID NO: 6 or an amino acid substitution at Ser30 of SEQ ID NO: 6.

14. An antibody molecule according to claim 7 that inhibits thrombin activity.

15. An antibody molecule according to claim 14 which does not inhibit hemostasis and does not cause bleeding in vivo.

16. The antibody molecule according to claim 7, wherein the LCDR1 has the amino acid sequence of SEQ ID NO: 7.

17. The antibody molecule according to claim 7, wherein the LCDR1 has the amino acid sequence of SEQ ID NO: 7 with an amino acid substitution at Asn5 of SEQ ID NO: 7 or has the amino acid sequence of SEQ ID NO: 7 with an amino acid substitution at Ser7 of SEQ ID NO: 7.

18. The antibody molecule according to claim 7, wherein the VL domain has the amino acid sequence of SEQ ID NO: 6.

19. The antibody molecule according to claim 7, wherein the VL domain has the amino acid sequence of SEQ ID NO: 6 with an amino acid substitution at Asn28 or an amino acid substitution at Ser30.

20. The antibody molecule according to claim 7, wherein the LCDR1 has the amino acid sequence of SEQ ID NO: 7 with one amino acid substitution.

21. The antibody molecule according to claim 7, wherein the antibody molecule is a monoclonal antibody.

22. The antibody molecule according to claim 7, wherein the antibody molecule is a minibody.

23. The antibody molecule according to claim 7, wherein the IgG constant region is an IgG1 or IgG4 constant region.

24. The antibody molecule according to claim 7, wherein the antibody molecule is a human antibody.

25. A pharmaceutical composition, comprising the antibody molecule according to claim 7 and a pharmaceutically acceptable carrier or excipient.

* * * * *

SEQUENCE LISTING

<160> NUMBER OF SEQ ID NOS: 9

<210> SEQ ID NO 1
<211> LENGTH: 622
<212> TYPE: PRT
<213> ORGANISM: Homo sapiens

<400> SEQUENCE: 1

```
Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
    50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
    130                 135                 140

Thr Thr His Pro Gly Ala Asp Leu Gln Glu Asn Phe Cys Arg Asn Pro
145                 150                 155                 160
```

```
Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
    210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
            245                 250                 255

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
        275                 280                 285

Asn Tyr Cys Glu Glu Ala Val Glu Glu Glu Thr Gly Asp Gly Leu Asp
        290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
            325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
            355                 360                 365

Asp Ala Glu Ile Gly Met Ser Pro Trp Gln Val Met Leu Phe Arg Lys
        370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
            435                 440                 445

Ile His Pro Arg Tyr Asn Trp Arg Glu Asn Leu Asp Arg Asp Ile Ala
        450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
        515                 520                 525

Pro Ile Val Glu Arg Pro Val Cys Lys Asp Ser Thr Arg Ile Arg Ile
        530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575
```

```
Pro Phe Asn Asn Arg Trp Tyr Gln Met Gly Ile Val Ser Trp Gly Glu
        580                 585                 590

Gly Cys Asp Arg Asp Gly Lys Tyr Gly Phe Tyr Thr His Val Phe Arg
        595                 600                 605

Leu Lys Lys Trp Ile Gln Lys Val Ile Asp Gln Phe Gly Glu
        610                 615                 620

<210> SEQ ID NO 2
<211> LENGTH: 125
<212> TYPE: PRT
<213> ORGANISM: Homo sapiens

<400> SEQUENCE: 2

Gln Val Gln Leu Ile Gln Ser Gly Ser Ala Val Lys Lys Pro Gly Ala
1               5                   10                  15

Ser Val Arg Val Ser Cys Lys Val Ser Gly Tyr Thr Leu Thr Glu Ala
            20                  25                  30

Ala Ile His Trp Val Arg Gln Ala Pro Gly Lys Gly Leu Glu Trp Met
        35                  40                  45

Gly Gly Leu Asp Pro Gln Asp Gly Glu Thr Val Tyr Ala Gln Gln Phe
    50                  55                  60

Lys Gly Arg Val Thr Met Thr Glu Asp Arg Ser Thr Asp Thr Ala Tyr
65                  70                  75                  80

Met Glu Val Asn Asn Leu Arg Ser Glu Asp Thr Ala Thr Tyr Tyr Cys
                85                  90                  95

Thr Thr Gly Asp Phe Ser Glu Phe Glu Pro Phe Ser Met Asp Tyr Phe
            100                 105                 110

His Phe Trp Gly Gln Gly Thr Val Val Thr Val Ala Ser
        115                 120                 125

<210> SEQ ID NO 3
<211> LENGTH: 10
<212> TYPE: PRT
<213> ORGANISM: Homo sapiens

<400> SEQUENCE: 3

Gly Tyr Thr Leu Thr Glu Ala Ala Ile His
1               5                   10

<210> SEQ ID NO 4
<211> LENGTH: 17
<212> TYPE: PRT
<213> ORGANISM: Homo sapiens

<400> SEQUENCE: 4

Gly Leu Asp Pro Gln Asp Gly Glu Thr Val Tyr Ala Gln Gln Phe Lys
1               5                   10                  15

Gly

<210> SEQ ID NO 5
<211> LENGTH: 16
<212> TYPE: PRT
<213> ORGANISM: Homo sapiens

<400> SEQUENCE: 5

Gly Asp Phe Ser Glu Phe Glu Pro Phe Ser Met Asp Tyr Phe His Phe
1               5                   10                  15
```

```
<210> SEQ ID NO 6
<211> LENGTH: 109
<212> TYPE: PRT
<213> ORGANISM: Homo sapiens

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Val Ser Ser Phe
            20                  25                  30

Leu Ala Trp Tyr Gln His Lys Pro Gly Gln Ala Pro Arg Leu Leu Ile
        35                  40                  45

Tyr Asp Ala Ser Ser Arg Ala Thr Asp Ile Pro Ile Arg Phe Ser Gly
50                  55                  60

Ser Gly Ser Gly Thr Asp Phe Thr Leu Thr Ile Ser Gly Leu Glu Pro
65                  70                  75                  80

Glu Asp Phe Ala Val Tyr Tyr Cys Gln Gln Arg Arg Ser Trp Pro Pro
                85                  90                  95

Leu Thr Phe Gly Gly Gly Thr Lys Val Glu Ile Lys Arg
            100                 105

<210> SEQ ID NO 7
<211> LENGTH: 11
<212> TYPE: PRT
<213> ORGANISM: Homo sapiens

<400> SEQUENCE: 7

Arg Ala Ser Gln Asn Val Ser Ser Phe Leu Ala
1               5                   10

<210> SEQ ID NO 8
<211> LENGTH: 7
<212> TYPE: PRT
<213> ORGANISM: Homo sapiens

<400> SEQUENCE: 8

Asp Ala Ser Ser Arg Ala Thr
1               5

<210> SEQ ID NO 9
<211> LENGTH: 10
<212> TYPE: PRT
<213> ORGANISM: Homo sapiens

<400> SEQUENCE: 9

Gln Gln Arg Arg Ser Trp Pro Pro Leu Thr
1               5                   10
```